United States Patent [19]

Jones

[11] 4,413,518

[45] Nov. 8, 1983

[54] APPARATUS AND METHOD FOR MEASURING THE EXTENSION OF BOLTS UNDER STRESS

[75] Inventor: Robert L. Jones, La Habra, Calif.

[73] Assignee: NDT Instruments, Inc., Huntington Beach, Calif.

[21] Appl. No.: 284,761

[22] Filed: Jul. 20, 1981

[51] Int. Cl.³ ............................................ G01N 29/00
[52] U.S. Cl. ........................................ 73/615; 73/597; 73/631
[58] Field of Search ................. 73/615, 597, 609, 610, 73/612, 616, 631, 900, 581, 761, 801; 364/508

[56] References Cited

U.S. PATENT DOCUMENTS

| | | | |
|---|---|---|---|
| 3,759,090 | 9/1973 | McFaul et al. | 73/610 |
| 3,918,294 | 11/1975 | Makino et al. | 73/581 |
| 3,969,810 | 7/1976 | Pagano | 73/581 |
| 3,985,022 | 10/1976 | Dileo | 73/629 |
| 4,102,205 | 7/1978 | Pies et al. | 73/631 |

*Primary Examiner*—Stephen A. Kreitman
*Attorney, Agent, or Firm*—Fischer, Tachner & Strauss

[57] ABSTRACT

A bolt elongation measurement apparatus and method for measuring the length of bolts of all sizes and shapes. The apparatus utilizes a microprocessor-based digital system including a binary counter which counts pulses generated by a high frequency oscillator during the time interval between the entry into the bolt of a first pulse and exit from the bolt of a second pulse derived from the reflection return of ultrasonic energy from the opposite end of the bolt. The count is applied to a computer for calculation of bolt length or of bolt stretch due to mechanical stress. The calculation also incorporates data input via thumbwheel switches and corresponding to material velocity, stress correction factor, measurement temperature, and thermal correction factor. A unique digital filtering algorithm ensures an accurate and stable measurement. The receiver of the apparatus overcomes the problem of spurious ultrasonic reflection characteristics of threaded bolts by means of a dual characteristic echo sensing circuit to deal with stress-induced pulse distortion and a unique gain contour circuit to deal with spurious echo pulses that are characteristic of threaded bolts.

51 Claims, 9 Drawing Figures

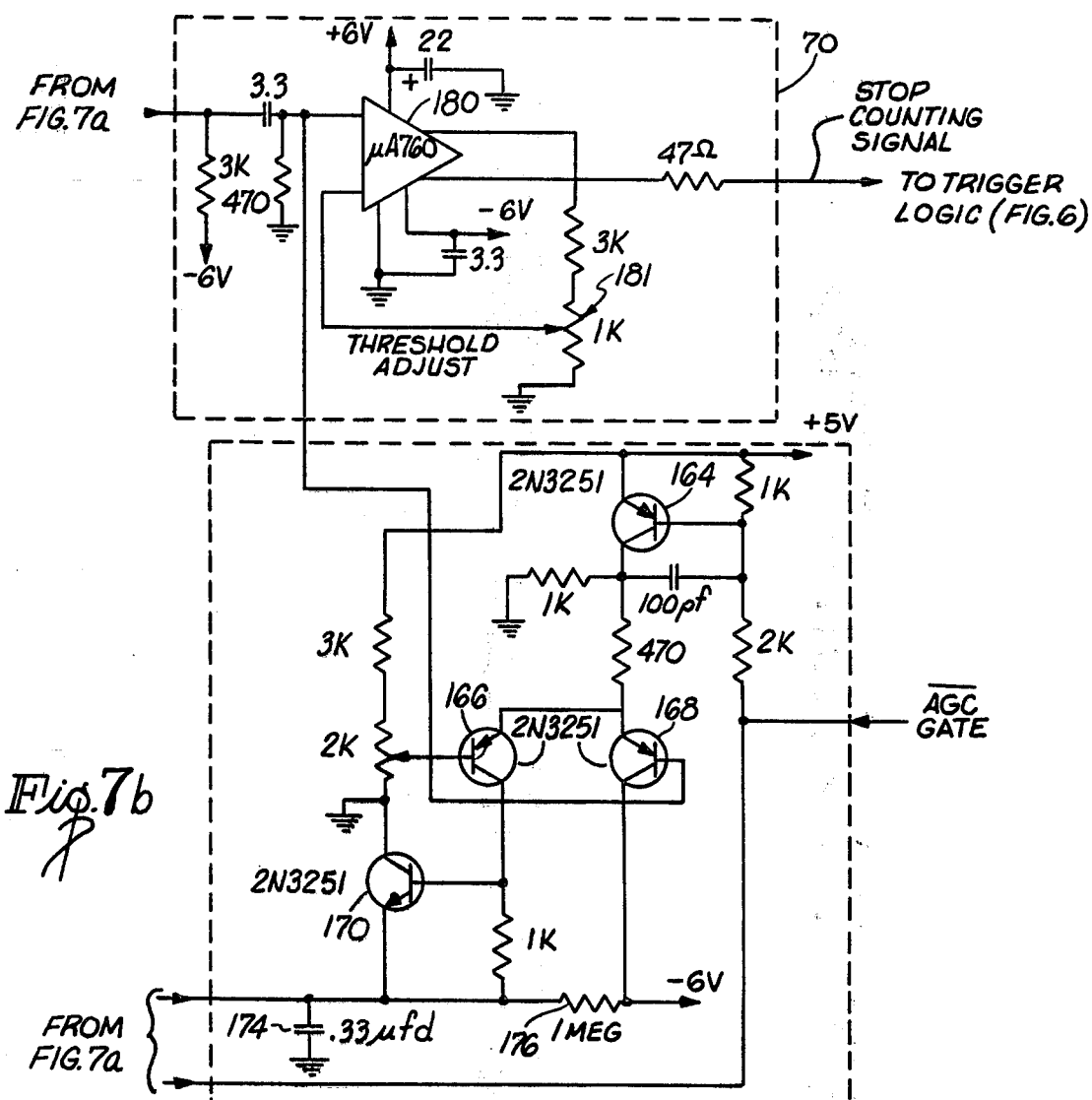
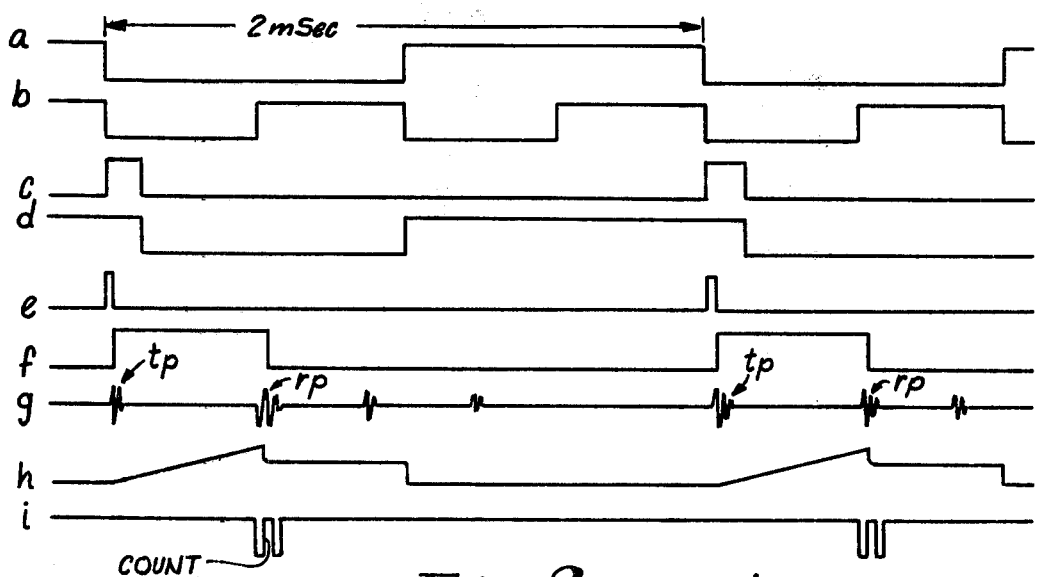
Fig. 7b
Fig. 8

APPARATUS AND METHOD FOR MEASURING THE EXTENSION OF BOLTS UNDER STRESS

BACKGROUND OF THE INVENTION

1. FIELD OF THE INVENTION

This invention relates generally to an ultrasonic length measuring system and more particularly, to an ultrasonic length measuring system which is extremely accurate and reliable in operation and which is especially adapted to measure the length of stressed bolts in situ.

2. PRIOR ART

It is generally well-known that there are numerous applications in which bolts as long as twelve feet and having cross-sectional diameters as large as six inches or more, are used in extremely high stress conditions to secure one part to another over a period of many years. For example, such large bolts may be used to secure the respective flanges of very large pipes or of valves in nuclear and refinery applications. Similarly, large bolts may be used to secure portions of a large vessel such as a nuclear reactor chamber or chemically reactive vessel where it is important that the bolts remain structurally viable despite the application of extremely high stresses over long periods of time. It is generally well-known that when such bolts are installed and tightened, it is important that the bolt's percentage of yield strength used be known to be sure that the bolt remains structurally viable. One method of determining the percentage of yield strength used is by measuring the bolt elongation resulting from the induced stress. For example, the best available high strength bolt material which has a yield strength of 240 Kpsi., will elongate 3.2 thousandths of an inch per inch of grip length at 40% of yield strength and 4.8 thousandths of an inch per inch of grip length at 60% of yield strength. This 40% to 60% yield strength range is considered generally acceptable in terms of structural viability for a tightened bolt. Thus, by measuring the elongation of a bolt as it is being tightened, the structural integrity of the bolt can be assessed and the optimum elongation can be obtained for a particular bolt material and length.

One prior art technique for measuring the actual length, and thus the elongation of bolts under stress, incorporates ultrasonic thickness measuring devices. Such devices include a transducer that is placed at one end of the bolt and an electronic gauge that responds to the reflections induced by the transducer. The gauge determines the distance between the first and second ends of the bolt on the basis of the time between reflections and the assumed velocity of the acoustic energy transmitted therethrough. Then, by comparing the measured length of the bolt under stress with a record of the actual length of the bolt unstressed, such as prior to its installation, an inspector can determine the change in length resulting from the continuous application of high stress and thereby ascertain whether or not the bolt is still of reliable structural integrity.

It will be recognized by those familiar with the art to which the present invention pertains, that the accuracy and resolution of the stressed bolt length measurement must be sufficiently high so that the change of bolt length computed therefrom provides a reliable indication of the actual elongation of the stressed bolt subject to measurement. Unfortunately, there are a number of factors that affect the nominal acoustical velocity that one might ordinarily rely upon to determine the corresponding bolt length for a given measurement. These factors include the effect on velocity resulting from the birefringent characteristics of a bolt under stress, the temperature under which the measurement is being made, and the coefficient of thermal expansion of the material being tested. Accordingly, these factors will detrimentally affect the accuracy of the length measurement unless means are provided for compensating for such factors. Unfortunately, prior art devices that rely upon the transmission of acoustic energy for time measurement which can then be related to the thickness of a material under test, do not provide means for compensating for such factors and would accordingly, yield an inaccurate result when applied to the particular measurement function described above. In addition to these disadvantages of the prior art, it is also to be noted that such prior art devices are particularly adapted to the measurement of thicknesses in the range of a few hundredths of an inch to sixteen to twenty inches maximum. Accordingly, such devices are not readily adapted to measuring bolt lengths that extend to seven feet or even longer. In addition to these relative disadvantages of the prior art, such prior art devices are not readily adapted to provide the measurement resolution required to display length changes that may be as small as 0.0001 inches that may ordinarily be required to measure relatively small changes in bolt lengths induced by moderate stresses as compared to their unstressed configuration.

Irrespective of bolt size, because of their relatively complex shapes from the standpoint of acoustic echo characteristics, bolts are inherently difficult to accurately measure. For example, a typical threaded bolt has a multitude of surfaces which tend to produce spurious echos that increase the likelihood of measurement error. No known prior art utilizing acoustic measurement techniques has satisfactorily solved this problem.

The following U.S. Patents are deemed to be relevant to the present invention:

| U.S. Pat. No. | Inventor |
| --- | --- |
| 3,354,700 | Schindler |
| 3,427,868 | Charbonnier et al |
| 3,605,504 | Kummer Jr. et al |
| 3,688,565 | Brech |
| 3,759,090 | McFaul et al |
| 3,918,294 | Makino et al |
| 3,962,910 | Spyridakis et al |
| 3,985,022 | Dileo et al |
| 4,064,735 | Hutchison et al |
| 4,104,778 | Vilet |
| 4,104,779 | Sigmund |
| 4,106,176 | Rice et al |
| 4,163,310 | Sigmund |
| 4,179,786 | Eshghy |

Of the above-identified patents some are relevant because they disclose measuring apparatus that utilize ultrasonic pulses for measuring the thickness of a test piece which may or may not be an elongated bolt and some are relevant because they disclose elongation measurement devices that are especially adapated to be used for measuring the elongation of bolts. The most relevant of the above-identified patents shall now be discussed in more detail.

The U.S. Pat. No. to Charbonnier et al (3,427,868) discloses an ultrasonic device for measuring the thickness of objects. The time period between a plurality of echo pulses is measured using a counter and a pulse duration multiplication circuit that permits the use of a low performance counter for measurement of the duration of a pulse that is proportional to the time interval between respective echos. Unfortunately, the Charbonnier patent does not disclose a device that is useable with elongated bolts, that is, a device that can overcome the special problems associated with length and elongation measurements as previously described. By way of example, Charbonnier does not disclose means for making temperature and stress factor corrections to the velocity of acoustic energy propagation, nor does it disclose means for measuring the nominal and elongated lengths of bolts that are as long as seven (7) feet or more. Furthermore, this patent does not disclose means for overcoming the special problems associated with noise and other reflection anomalies that are unique to ultrasonic measurement of elongated structures such as very long bolts.

Another form of ultrasonic thickness measuring system which utilizes a counter for measuring the interval between a transmitted burst and a reflected signal is disclosed by Kumer Jr. et al in U.S. Pat. No. 3,605,504. However, Kumer Jr. et al also fails to disclose a system which can overcome all the special problems associated with measuring the nominal length and elongation of a very long bolt.

The U.S. Pat. No. to McFaul et al (3,759,090) discloses an analog-type ultrasonic extensometer for measuring the elongation of a bolt. A meter is used to indicate when the time interval between the transmitted signal and the echo pulse from the far end of the bolt equals a preselected period of time which corresponds to a predetermined bolt length including bolt elongation due to stress. Although McFaul et al recognize the effects of temperature and stress on the accuracy of such measurements, they fail to disclose a convenient and accurate way of adjusting the measuring device to compensate for temperature and fail to disclose any means for adjusting for the effects of the velocity of acoustical energy in a stress bolt as compared to the velocity in an unstressed bolt by dismissing that change in velocity as being negligible and imperceptible in the meter readings of their device.

The U.S. Pat. No. to Makino et al (3,918,294) discloses a method for measuring the actual forces existing in bolts by applying an ultrasonic wave to the article under test to generate forced oscillations within the article, measuring a first natural frequency before the application of axial force, and measuring a second natural frequency subsequent to the application of axial force. Makino et al then determine the difference between those two frequencies and compare that difference against calibration data to determine the axial force during an actual test.

The U.S. Pat. No. to Dileo et al (3,985,022) discloses an ultrasonic measuring device which employs digital counting means and which provides an output indication of thickness of a work piece when the accumulated counts provided during successive time intervals of transmitted search pulses reaches a value that corresponds to a quantity of such search pulses which is commensurate with the acoustic velocity of the work piece. However, as with other prior art discussed previously, Dileo et al do not disclose means for accurately compensating for variations in acoustic velocity resulting from temperature and/or stress, nor do they disclose means for overcoming the special problems associated with measuring lengths of elongated bolts as previously described and as will be more fully understood hereinafter.

SUMMARY OF THE INVENTION

The present invention overcomes or substantially reduces the aforementioned disadvantages of the prior art by providing an apparatus and process for measuring the length of stressed bolts to extreme accuracies, and includes means for inclusion of correction factors dependent upon the stressed condition of the bolt, the temperature in which the measurement is being made and the thermal correction coefficient of the material under test, to provide a length or length difference measurement which is based upon an accurate representation of the actual velocity of acoustical energy in the stressed bolt being tested. The apparatus utilizes a microprocessor-based digital system including a binary counter which is connected to an extremely high frequency oscillator. The counter is adapted to provide a high resolution count dependent upon the time interval between a first pulse entering the outer surface of the bolt under test at the probe input end, and a second pulse which is derived from the reflection return of the ultrasonic energy from the opposite end of the bolt.

The count is applied to a microprocessor-based computer for calculation of bolt length. The calculation also utilizes data input via thumbwheel switches and corresponding to material velocity, stress correction factor, measurement temperature, and thermal correction coefficient. In addition, a switch is provided for selecting digital display of either full bolt length or the difference between full elongation and an initial length which may be entered via an additional thumbwheel switch after it is measured using the invention or after it is copied from tabulated data. A unique digital filtering algorithm is used to ensure an accurate and stable measurement.

A novel receiver circuit is utilized to overcome the unique acoustical characteristics of threaded bolts. More specifically, a dual characteristic echo sensing circuit is used to ensure measurement accuracy despite acoustic pulse distortion that results from bolt stress, and a special gain contour circuit is used to further ensure measurement accuracy despite spurious acoustic echos that arise in threaded bolts.

Thus, the present invention provides a novel bolt elongation measurement apparatus and method which are designed to accommodate threaded bolts of virtually all shapes and sizes including very long bolts, with extreme measurement accuracy despite problems unique to such bolts. Stress and temperature induced inaccuracies of prior art devices are readily compensated for by means of thumbwheel switch entered correction factors and a microprocessor-based computer. Bolt stress and geometry induced inaccuracy of prior art devices is also readily compensated for in the present invention by a receiver designed to compensate for acoustic echo pulse distortion and to ignore anomalous echos as will be more fully understood hereinafter.

OBJECTS

It is therefore a principal object of the present invention to provide an apparatus and method for measuring the extension of bolts under stress and which apparatus and method overcome or substantially reduce the aforementioned disadvantages of prior art devices.

It is another object of the present invention to provide an apparatus for measuring the length of bolts as long as seven feet or more and which provides means for achieving increased accuracy of measurement by including input signals representative of correction factors, the omission of which would otherwise render the result highly inaccurate.

It is still a further object of the present invention to provide a portable electrical device for measuring the elongation of stressed bolts in situ and which includes means for entering data representative of nominal length, nominal acoustic velocity, an acoustic velocity stress correction factor, temperature of the measurement, and thermal expansion coefficient; to provide a highly accurate digital representation of the bolt elongation.

It is still a further object of the present invention to provide a microprocessor-based portable electronic instrument for measuring the elongation of stressed bolts in situ (based upon the time of traversal of an acoustic pulse along the length of the bolt) in which the microprocessor is adapted to automatically incorporate acoustic velocity, stress correction factor, measurement temperature and thermal expansion coefficient in the calculation of the bolt elongation.

It is still another object of the present invention to provide a bolt extensometer which employs a novel receiver circuit to overcome the unique acoustical characteristics of a long threaded bolt. More specifically, the receiver circuit employs a dual characteristic echo sensing circuit to compensate for pulse distortion anomalies and a gain contour circuit to overcome spurious acoustic echo anomalies that are indigenious to threaded bolts and which would otherwise preclude the accurate measurement of bolt elongation.

BRIEF DESCRIPTION OF THE DRAWINGS

The above-noted objects and advantages of the present invention as well as additional objects and advantages thereof will be more fully understood hereinafter as a result of the detailed description of a preferred embodiment of the invention taken in conjunction with the accompanying drawings in which:

FIG. 7, comprising FIGS. 7a and 7b, is a schematic diagram of the receiver portion of the invention; and FIG. 8 is a timing diagram illustrating the respective timing of nine selected signals utilized in the invention.

DETAILED DESCRIPTION OF A PREFERRED EMBODIMENT

Figure 1:
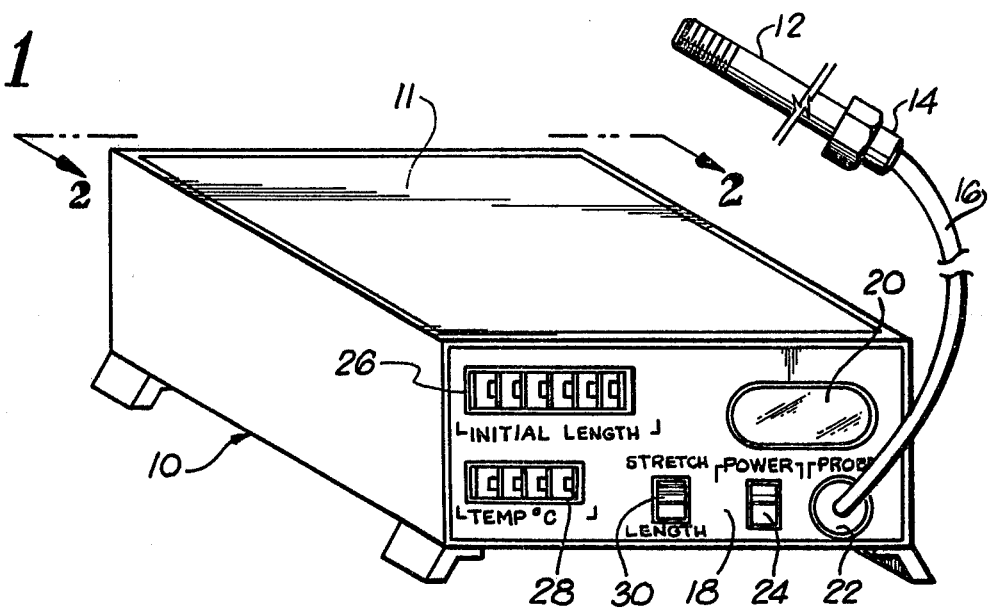
FIG. 1 is an isometric view of the apparatus of the invention showing the front panel thereof and illustrating the manner in which the invention is used to measure the length of a bolt.
Figure 2:
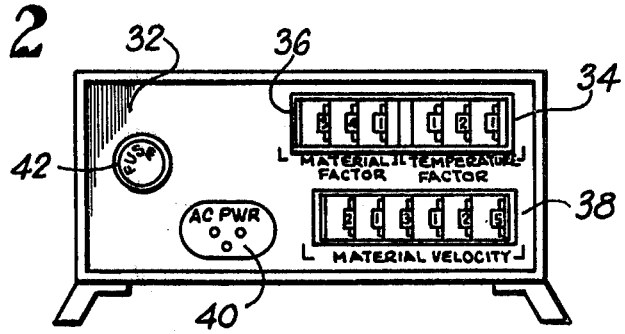
FIG. 2 is a plan view of the rear panel of the apparatus taken along lines 2—2 of FIG. 1.

The physical appearance of the apparatus of the present invention may be best understood by reference to FIGS. 1 and 2 which illustrate the overall assembly as well as the front and rear panels, respectively. As seen in FIG. 1, the portable electronic bolt elongation measurement apparatus 10 comprises a self-contained portable housing 11 which enables onsight field measurements of the elongation of bolts such as bolt 12 in the manner illustrated. A suitable transducer 14, which is well-known in the art of ultrasonic thickness measuring devices, is normally applied at about the center of the head of the bolt 12 typically using some couplant material such as oil to assure firm, continuous contact between the transducer and the bolt. In bolt length measurement applications it may be advantageous to utilize a transducer which comprises a magnetic material so that the operator may secure the transducer to the bolt by means of magnetic attraction and thus free both of his hands for operation of the apparatus. The transducer is connected to apparatus 10 by a suitable coaxial cable 16 whereby transmitted pulses may be transferred between the apparatus and the transducer for application to the bolt and echo pulses transmitted from bolt to apparatus for subsequent reception by the contained receiver as will be described herein in more detail.

Apparatus 10 includes a front panel 18 which, in the preferred embodiment of FIG. 1, includes a liquid crystal display 20, a probe connector 22, a power switch 24, an initial length thumbwheel switch array 26, a temperature thumbwheel switch array 28, and a length/stretch selection switch 30. Apparatus 10 also includes a rear panel 32 which is illustrated in FIG. 2. On rear panel 32 are mounted a temperature factor thumbwheel switch array 34, a correction factor thumbwheel switch array 36, and a material velocity thumbwheel switch array 38. Also shown are AC power connector 40 and line fuse 42. It is to be noted that the instrument of the present invention may be operated on either AC power provided through connector 40 through a suitable line cable, or by means of internal rechargeable batteries which provide various DC voltages that are required and that are noted in the diagrams of FIGS. 5, 6 and 7.

The preferred embodiment of the apparatus of the invention illustrated in FIGS. 1 and 2 utilizes an ultrasonic pulse frequency of 5 MHz. with a 9 MHz. bandwidth. The apparatus may be selected to operate in either English or metric units and provides a bolt length measurement range of between 1 inch and 99 inches or between 2.5 centimeters and 99 centimeters. It also measures bolt elongation (or stretch) anywhere within the range of 0 to 99 inches or 0 to 99 centimeters. The digital resolution is plus or minus 0.0001 inch or plus or minus 0.0003 meters. The instrument error is less than plus or minus twenty parts per million plus or minus one digit and utilizes a six digit liquid crystal display 20 as seen on the front panel 18 in FIG. 1.

All of the multi-digit thumbwheel switches provide a binary coded decimal (bcd) outputt as will be described hereinafter in more detail. The initial length switch array 26 is a six digit entry device with two digits to the left of the decimal point and four to the right. Temperature entry switch array 28 provides four entries including a (sign) bit and a two and one half digit switch entry for temperatures in the range of −199° C. to +199° C., to the nearest degree. The material velocity switch array 38 on the rear panel is a six digit thumbwheel switch array in which velocity may be entered in either inches per microsecond or centimeters per microsecond. By way of example, a typical material correction factor for rolled aluminum is 0.253000 inches per microsecond.

The temperature factor switch array 34 is a three digit entry thumbwheel switch which provides for entry of numbers in the range of 000. to 999. parts per million per degree centigrade, which may be used to enter the temperature factor of the bolt material to automatically compensate for the difference in temperature during the current measurement as represented by switch array 28 on the front panel, and a reference temperature of 25° C. or other selected reference temperature encountered during a prior measurement.

The initial length thumbwheel switch arrary 26 is a six digit entry switch which provides for initial bolt length entry data in the range of 0 to 99.9999 inches or centimeters. The velocity correction factor thumbwheel switch array 36 is a three digit range input device which provides for a correction multiplier in the range of 0.000 to 0.999.

Figure 3:
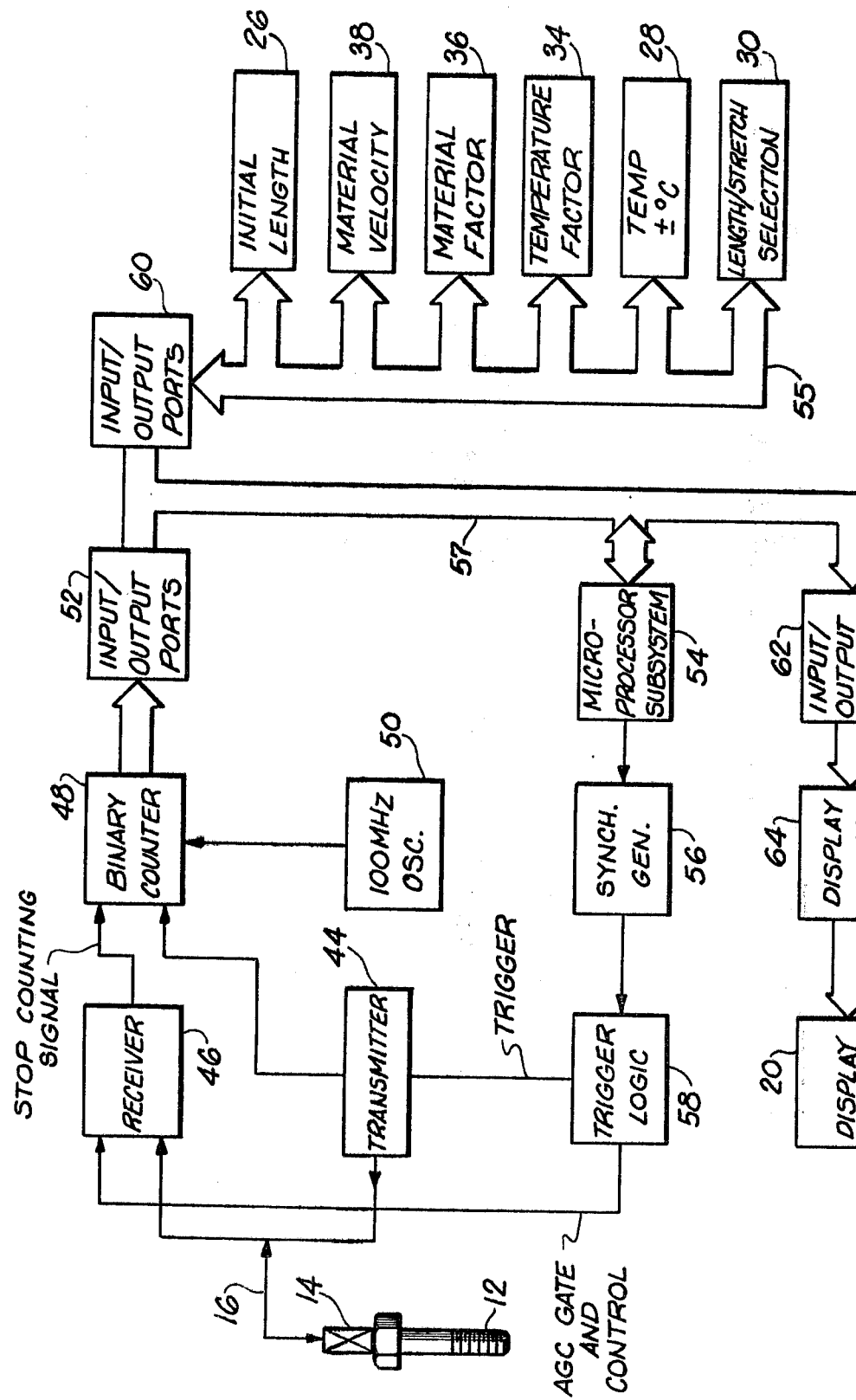
FIG. 3 is a block diagram of the apparatus of the invention.

An overall block diagram of the apparatus of the present invention is illustrated in FIG. 3. Included are a transmitter 44 and a receiver 46 both connected to transducer 14 via cable 16 for transmitting ultrasonic pulses into bolt 12 from one end thereof and for receiving the echo pulses generated thereby. The system also comprises a binary counter 48, a high frequency oscillator 50, input-output ports 52, a microprocessor subsystem 54, a synchronization generator 56, and trigger logic 58. In addition, all of the previously identified thumbwheel switch arrays are connected to microprocessor subsystem 54 by means of inut-output ports 60 and display 20 is interconnected to the microprocessor subsystem 54 by means of input-output ports 62 and display driver 64.

The timing of the measurement process performed by the apparatus of FIG. 3 is controlled by a 2 MHz. clock signal generated by the microprocessor subsystem 54. The clock signal is applied to the synchronization generator 56 and trigger logic 58 to develop a trigger signal having a 2 millisecond period that is applied to transmitter 44 for generating an ultrasonic pulse 500 times a second. Shortly after the application of the transmission pulse into bolt 12, a counter gate signal is applied to binary counter 48 in response to which binary counter 48 begins counting the number of pulses produced by 100 MHz. oscillator 50. Binary counter 48 continues to count those pulses until a stop counting signal is generated by receiver 47 in response to reception of the first valid echo signal reflected from the far end of bolt 12 in response to the transmitted pulse. Accordingly, the final count generated by binary counter 48 in response to each transmitted pulse into bolt 12, represents the time it takes for the transmission pulse to travel the length of bolt 12, reflect off the end of the bolt and again travel the length of the bolt back to transducer 14. By converting that count into a time of travel and incorporating the known material velocity of the bolt, the length of the bolt is measured to an accuracy dependent upon the stability of oscillator 50 and resolution of counter 48. This process is repeated every 2 milliseconds. A large number of such counts (i.e. 160) are averaged over a fraction of a second and that average further improves the precision of the measurement. A unique binary filtering process described below assures a reliable averaging process that is free of erroneous counts. Each binary count produced by binary counter 48 in response to a transmitted pulse is transferred to input-output ports 52 and thereafter into appropriate portions of memory circuits of microprocessor subsystem 54 as will be hereinafter more fully understood.

As previously discussed, the precision of a bolt elongation measurement using ultrasonic techniques is highly dependent upon the inclusion of correction factors which account for changes in material velocity as a function of stress and changes in length as a function of temperature. The present invention is capable of incorporating such correction factors in the measurement process to provide increased accuracy and precision for the unique characteristics of bolts under stress. The means by which these factors are entered into the measurement process have been alluded to earlier, namely, the thumbwheel switch arrays located on the front panel 18 and rear panel 32 of apparatus 10 shown in FIGS. 1 and 2. In FIG. 3 the blocks on the right-side of the figure, consisting of initial length array 26, material velocity array 38, material factor array 36, temperature factor array 34, temperature array 28, and length/stretch selection switch 30, are all connected to a common data bus 55. Bus 55 transfers binary coded decimal representations of those switch positions to microprocessor subsystem 54 via input-output ports 60. An additional input-output port 62 provides suitable interface between microprocessor subsystem 54 and digital display 20 which is driven by display drivers 64. The various input-output ports 52, 60 and 62 are interconnected to the microprocessor subsystem 54 by means of a data bus 57 as seen in FIG. 3. It is to be noted that trigger logic 58 in addition to providing a trigger signal to transmitter 44 also provides an AGC gate signal and a control signal to receiver 46 for purposes that will be more fully understood hereinafter.

As previously indicated, the difficult problems associated with accurate and precise measurement of bolt elongation that have been solved by the present invention relate also to anomolous characteristics of the reflections of the ultrasonic pulses that are transmitted by transducer 14 into bolt 12. These problems relate to the distortion of the pulse wave shape which renders it more difficult to utilize a consistent characteristic of the reflected pulse to generate the stop counting signal shown previously in conjunction with FIG. 3. In addition, the peculiar acoustical characteristics of a threaded bolt typically results in the production of a plurality of echo signals from one transmitted pulse. One particular problem solved by the present invention and otherwise especially troublesome in measuring the time period elapsed between the transmitted pulse and the first received echo pulse, is the typically anomolous behavior of the secondary echo pulses in that their amplitudes often exceed the amplitude of the first generated valid echo pulse.

Figure 4:
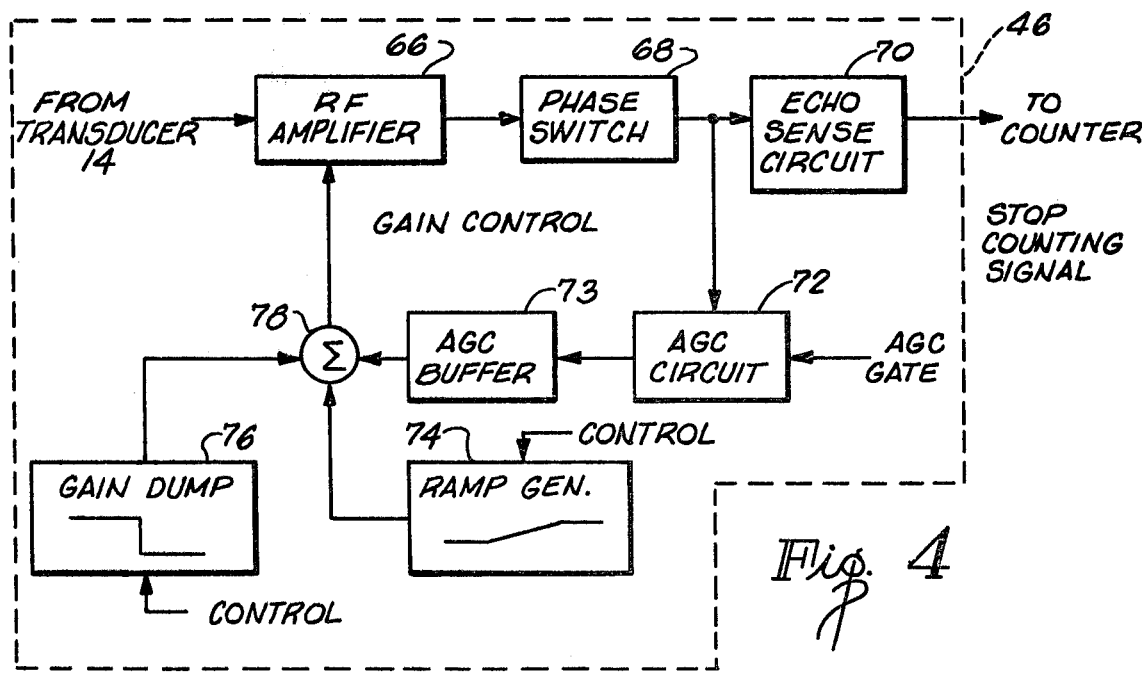
FIG. 4 is a block diagram of the receiver portion of the invention.

The receiver of the present invention utilizes a unique echo sense circuit to overcome the pulse distortion problems described above. It also utilizes a unique gain control circuit to overcome the effects of high amplitude anomolous secondary echo pulses as described above. FIG. 4 provides a simplified block diagram of the receiver portion of the invention. Receiver 46 comprises an RF amplifier 66, a phase switch 68, an echo sense circuit 70, an AGC circuit 72, an AGC buffer 73, a ramp generator 74, a gain dump circuit 76 and a junction 78 for summing the output signal of the AGC circuit, ramp generator and gain dump circuit. The combined signal is input as a gain control signal into RF amplifier 66.

As seen in FIG. 4, the signal from transducer 14 is applied to RF amplifier 66. Amplifier 66 consists of a dual stage amplifier circuit capable of providing up to 70 db gain. The amplified signal is passed into phase switch 68 which provides means for selecting either polarity of the signal generated at the output of RF amplifier 66 depending upon which signal phase provides the best wave form for accurate echo pulse detection by echo sensor circuit 70. The output signal of echo sensor circuit 70 is the stop counting signal which is transmitted to the binary counter as previously indicated in conjunction with FIG. 3. The output of phase switch 78 is also connected to the AGC circuit 72 for adjusting the gain bias level to an appropriate magnitude for the nominal amplitude of the reflected echo ultrasonic pulse. AGC circuit 72 performs this bias adjustment during the occurrence of an AGC gate signal transferred from the trigger logic 58 discussed previously in conjunction with FIG. 3 and the output signal of the AGC gate circuit 72 is applied to a buffer 73. The output of buffer 73 is connected to junction 78. The outputs of ramp generator 74 and gain dump circuit 76 are also connected to junction 78 to provide a gain control signal into RF amplifier 66, which signal is the sum of the outputs of AGC buffer 73, ramp generator 74, and gain dump circuit 76, respectively.

A more detailed description of the hardware portion of the present invention shall now be described in conjunction with FIGS. 5-7.

Figure 5:
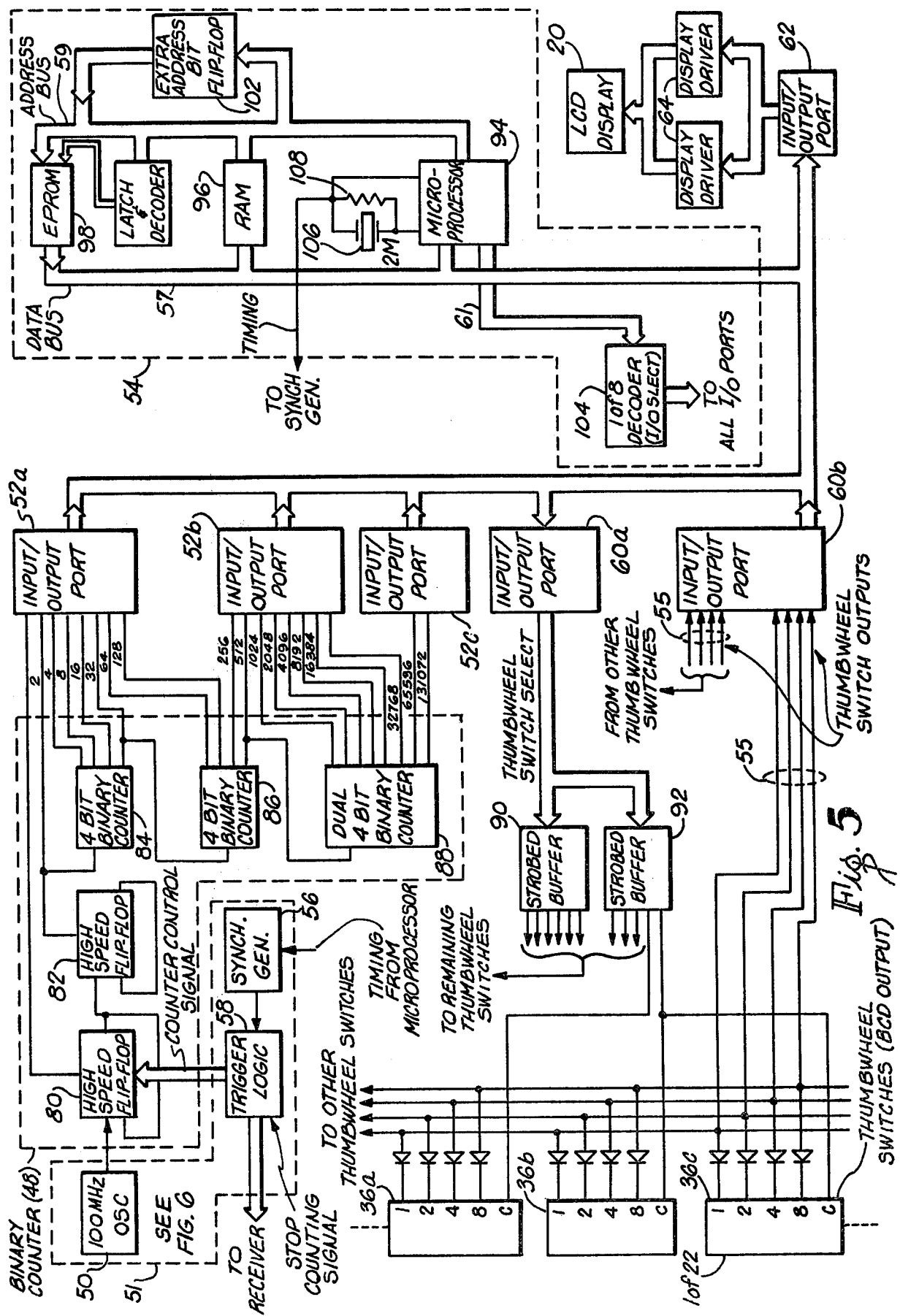
FIG. 5 is a partially schematic and partially block diagram of the digital portion of the invention.

Referring to FIG. 5 there is shown the individual circuit elements of the binary counter 48, the microprocessor subsystem 54, the thumbwheel switch arrays in which array 36 is included as an illustrative example, the display 20, display drivers 64 and the interconnecting buses and input-output ports for interfacing with the microprocessor subsystem. A portion of FIG. 5 including oscillator 50, synchronous generator 56 and trigger logic circuit 58 is included in block form but further described in conjunction with the more detailed schematic diagram of FIG. 6.

As seen in FIG. 5, binary counter 48 comprises a pair of high speed flip-flops, 80 and 82, a pair of 4-bit binary counters 84 and 86, and a dual 4-bit binary counter 88. High speed flip-flops 80 and 82 may, be way of example, both be contained on a single 74F74 Schottky TTL chip containing a dual D-flip-flop which is capable of responding to clock frequencies as high as 145 MHz. Such chips are available from the Fairchild Camera and Instrument Corporation of Mountainview, Calif. and are described at pages 3-5 of that company's publication entitled "FAIRCHILD ADVANCED SCHOTTY TTL", copyright 1979. The 4-bit binary counters 84 and 86 may, be way of example, be model SN74LS293 4-bit binary counters manufactured by Texas Instruments Incorporated of Dallas, Texas and described at page 4-423 etcetera of that company's publication entitled "TTL DATA BOOK FOR DESIGN ENGINEERS, SECOND EDITION", copyright 1976. Dural 4-bit binary counter 88 may, by way of example, be a model CD4520B COS/MOS dual binary up-counter manufactured by RCA Corporation and described in that company's publication entitled "RCA SOLID STATE COS/MOS INTEGRATED CIRCUITS", copyright 1978, beginning at page 292. The flip-flops 80 and 82 and counters 84, 86 and 88 are interconnected to provide a binary counter having an 18 bit capacity of which the most significant bit corresponds to a count of 128K.

The 18 output lines of binary counter 48 are supplied as input signals to input-output port 52 consisting of individual ports 52a, 52b, and 52c as shown in FIG. 5. In the preferred embodiment of the apparatus, each such input-output port comprises a model CDP1852 8-bit input/output port manufactured by RCA Corporation and described beginning at page 112 of their publication entitled "RCA SOLID STATE COS/MOS MEMORIES, MICROPROCESSORS, AND SUPPORT SYSTEMS", copyright 1979. All such input/output ports including input/output ports 60a and 60b that are used to interface the thumbwheel switches to the microprocessors sub-system 54 and input/output port 62 that is used to interface the display and display drivers to the microprocessor sub-system, are identical chips selected primarily because of their capability with the microprocessor sub-system as will be described hereinafter in more detail. Binary counter 48 counts at a constant rate in response to 100 MHz. oscillator 50, which is a highly stable and accurate quartz controlled oscillator. However, counter 48 begins and ends the counting process in response to counter control signals generated by trigger logic 58 in response to sync generator 56, the timing of which is controlled by microprocessor 94 as will be described in further detail below and also in response to the stop counting signal received from receiver 46 as will also be described further below. Thus, the period during which binary counter 48 is permitted to count the output derived from 100 MHz. oscillator 50 is dependent upon the time interval between the occurrence of the transmitted ultrasonic pulse which enters the head of bolt 12 and the reception of the first valid echo pulse traveling back along bolt 12 to the receiver 46 (see FIG. 3).

It will be observed that input/output ports 52 provide a count input to the microprocessor based sub-system 54 that corresponds to the nominal traversal time of an ultrasonic pulse transmitted into and received back along bolt 12. The other principal input to microprocessor sub-system 54 for the purpose of calculating an accurate measurement of bolt length or bolt elongation, is provided by the aforementioned plurality of thumbwheel switch arrays. The three thumbwheel switches comprising correction factor thumbwheel switch array 36 are shown in FIG. 5 as an illustration of the manner in which all such thrumbwheel switches are interconnected to microprocessor sub-system 54.

There are a total of 22 such thumbwheel switches comprising the various arrays discussed previously. Each such switch is a digital thumbwheel switch having a binary coded decimal (BCD) output. Each output terminal of the thumbwheel switch is tied into the corresponding output of other thumbwheel switches in either one of two 4-wire buses that are applied to the eight input terminals of input/output port 60b. In addition, each thumbwheel switch includes a common connection C which is connected to an output of a strobe buffer 90 or 92, the input terminals of which are connected to input/output port 60a. Thus, input/output port 60a, in response to signals on the data bus of microprocessor sub-system 54, selects any two of the plurality of thumbwheel switches by grounding the corresponding common lines through pull-up resistors (not shown) whereby the output signals on the corresponding BCD terminals of those selected thumbwheel switches are applied to the input terminals of input/output port 60b for transfer to the microprocessor sub-system 54. In this manner microprocessor sub-system 54 selects and receives at appropriate times during the oeration of the apparatus, any of the correction factors and other information previously inserted into the respective thumbwheel switch arrays described previously. Strobe buffers 90 and 92 may be, by way of example, RCA CD4502B COS/MOS strobed hex inverter/buffers which are discussed beginning at page 268 of the aformentioned RCA publication on COS/MOS integrated circuits.

Thus it will be seen that the input/output ports 52a, 52b, 52c and 60b, in combination, provide all the requisite input signals to microprocessor sub-system 54 for measuring a corrected time interval of ultrasonic pulse travel through bolt 12 including correction factors entered into a plurality of thumbwheel switches to permit compensation for temperature and stressed-induced errors that would otherwise detrimentally affect the accuracy of the measurement process.

The remainder of FIG. 5 includes microprocessor sub-system 54 and the display portion of the apparatus, tthe later of which includes input/output port 62, display drivers 64, and LCD display 20. Input/output port 62 is also an RCA model CDP1852 8-input/output port, the input terminals of which are connected to the data bus to which all other input/output ports are connected. The output terminals of input/output port 62 are connected to the pair of 4-digit decoded display drivers. Drivers 64 may, by way of example, be Intersil model ICM7211 devices which drive display 20 which is a liquid crystal model 60D9R05JH manufactured by General Electric Corporation.

Microprocessor sub-system 54 comprises microprocessor 94, random access memory (RAM) 96, eraseable, programmable read-only memory (EPROM) 98, latch and decoder 100, flip-flop 102, and decoder 104.

Microprocessor 94 may, by way of example, be an RCA model CDP1802 microprocessor which is described in detail beginning at page 17 of the aforementioned RCA publication of COS/MOS MEMORIES, MICROPROCESSORS, AND SUPPORT SYSTEMS. The random access memory (RAM) may, by way of example, be an RCA model CDP1824 32-word by 8-bit static random access memory described beginning at page 69 of said publication. Eprom 98 may, by way of example, be a Texas Instruments model TMS2516JL 16-K eraseable, programmable, read-only memory having a 20 48 X8 organization as described at page 200 of the Texas Instruments publication entitled "THE MOS MEMORY DATA BOOK FOR DESIGN ENGINEERS", copyright 1977. Latch and decoder 100 may, by way of example, be an RCA model CDP1859 type COS/MOS 4-bit latch with decode as described beginning at page 156 of the aforementioned RCA publication. Extra address bit flip-flop 102 may, by way of example, be an RCA model CD4013A dual D-type flip-flop, and one of eight decoder 104 may, by way of example, be an RCA model CDP1853 N-bit one of eight decoder as described beginning at page 119 of the aforementioned RCA publication.

Microprocessor 94 is an eight-bit bi-directional data bus, eight-bit memory address architecture microprocessor. However, because Eprom 98 utilizes a 2K memory structure requiring eleven address bits on address bus 59, three additional address bits are generated, two by latch and decoder 100 and one by extra address bit flip-flop 102 as seen in the right portion of FIG. 5. Data bus 57, in addition to comprising eight data lines that interconnect the microprocessor with RAM 96 and Eprom 98 and all interconnecting input/output ports, also includes a read level signal which is used to indicate the direction of data transfer during input/output instructions. An additional bus 61 interconnects microprocessor 94 and one of eight decoder 104 and includes three input/output command signals as well as a timing pulse signal, all of which are used to select the appropriate input/output port at the appropriate time during the measurement process as will be more fully hereinafter understood as a result of the description of the software portion of the invention. Cycle timing for microprocessor sub-system 54, as well as for the remainder of the logic circuits of the invention, is derived from 2 MHz. crystal 106 and 10 MegOhm resistor 108 which are connected in parallel to the clock terminal of microprocessor 94 for generating a 2 MHz. clock signal. This 2 MHz. signal is transferred to synchronization generator 56 for controlling the counting cycle as will now be described in conjunction with FIG. 6.

Figure 6:
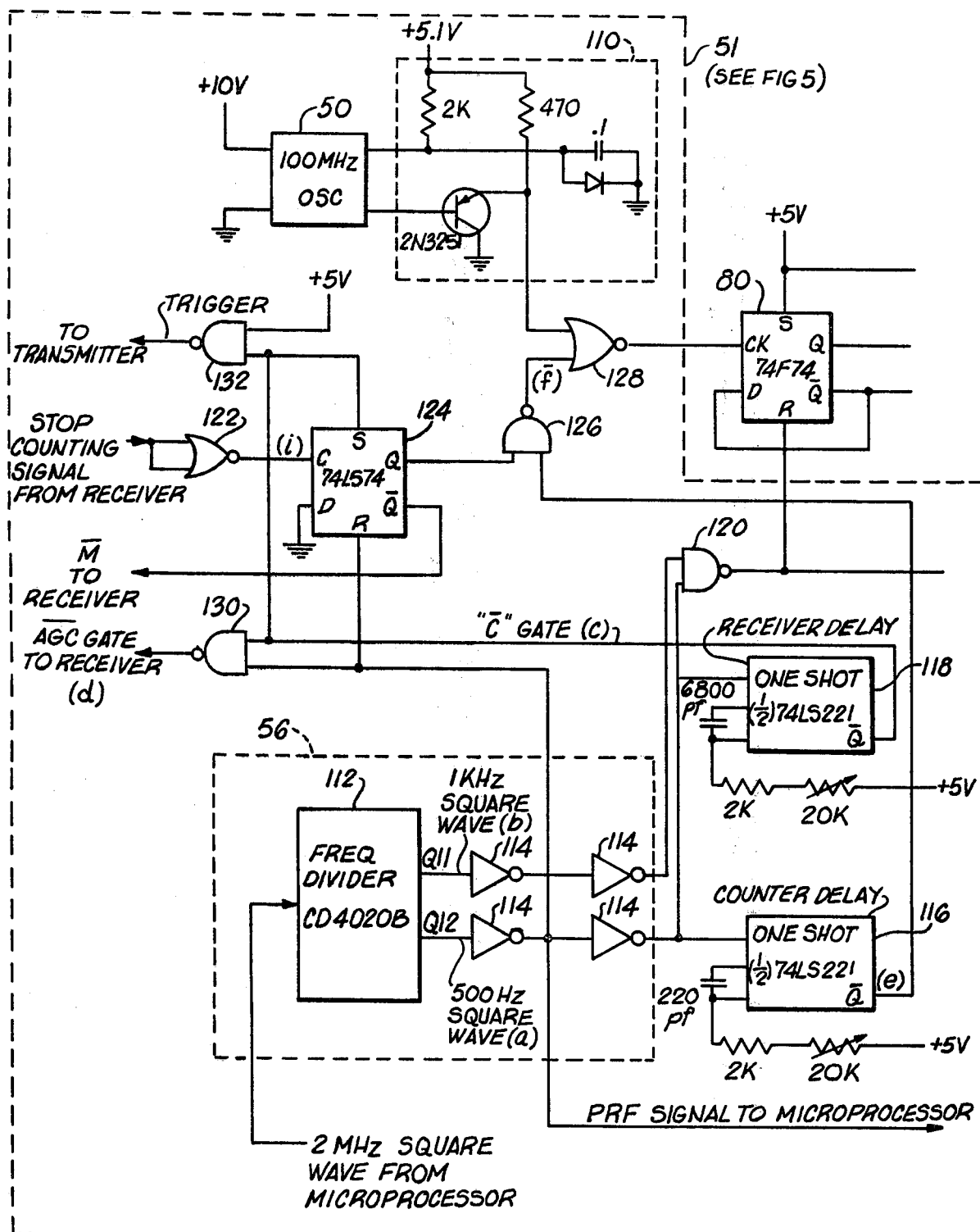
FIG. 6 is a schematic diagram of those features of the digital portion of the invention shown in block form in FIG. 5.

In FIG. 6 it will be seen that 100 MHz. oscillator 50 is applied to an emitter follower output circuit 110 which utilizes a 2N3251 transistor. The emitter output is applied to a NOR gate 128, the output of which is applied to the clock terminal of the first high speed flip-flop 80 of binary counter 48. The second input to NOR gate 128 is derived from the output of NAND gate 126. Those familiar with the art to which the present invention pertains will understand that only when the output signal logic state of NAND gate 126 is in a zero or false state can the variation in logic states of the output of circuit 110 be transferred as a series of 100 MHz. frequency pulses to the clock terminal of high speed flip-flop 80 of the counter. Conversely, when the output signal at the output terminal of NAND gate 126 is in a high or true state, the output of OR gate 128 will remain fixed irrespective of the changes of the signal derived from 100 MHz. oscillator 50. Accordingly, NAND gate 126 and NOR gate 128 provide a gating means to control the application of high frequency pulses to the binary counter. Thus, only when both input terminals to NAND gate 126 have signals in a one or true state can counter 48 be activated. One of those two terminals is connected to the Q output of D-type flip-flop 124 and the other terminal of NAND gate 126 is connected to the Q output of monostable multivibrator or one shot 116. One shot 116 provides an adjustable delay of nominally 200 nanoseconds in initiation of counting in binary counter 48 to compensate for ultrasonic pulse delays in the circuit transducer and transducer cable so that the counter starts counting precisely when the transmitted ultrasonic pulse starts its travel into the head of bolt 12. An additional timing delay is provided by one shot 118 for the purpose of inhibiting receiver 46 so that the receiver remains insensitive to the ringing produced by the generation of the transmitted ultrasonic pulse into bolt 12. This delay is also adjustable and is typically in the range of 4 to 8 microseconds.

Logic timing for the circuits of FIG. 6 is controlled by synchronization generator 56 which comprises a frequency divider chip 112 and a plurality of logic inverters 114 which are used to provide the appropriate signals for the remaining logic circuits of trigger logic 58. Frequency divider 112 may be, by way of example, an RCA model CD4020B COS/MOS 14-stage ripple-carry binary counter/divider which is described beginning at page 107 of the aforementioned RCA publication. Frequency divider 112 receives input pulses at a 2 MHz. frequency from the timing output of microprocessor 94 as discussed previously in conjunction with FIG. 5. Only the 11th and 12th output stages of frequency divider 112 are used in the present invention, the 11th stage providing a 1 kiloHertz frequency output signal derived from the 2 MHz. input signal from microprocessor 94. The 1 kiloHertz and 500 Hertz signals are applied to all of the reset terminals of the counting elements of binary counter 48 via NAND gate 120 to reset the counters every 2 milliseconds. The 500 Hertz output signal of frequency divider 112 is applied to the A input terminals of one shots 116 and 118, both of which reside on a single Texas Instruments model 74LS221 chip entitled DUAL MONOSTABLE MULTI-VIBRATORS WITH SCHMITT-TRIGGER INPUTS described beginning at page 6–68 of the Texas Instruments publication entitled "THE TTL DATA HANDBOOK FOR DESIGN ENGINEERS", copyright 1976. Thus it will be seen that the counting process is repeated every two milliseconds and that the counting process can take place only during the first 1 millisecond of that period at which time the counters remain stable for 500 microseconds to allow data transfer to the microprocessor. The reset pulse is then applied for the last 500 microseconds of the time interval.

Each 2 millisecond cycle is initiated upon the generation of a pulse at the Q-12 terminal of frequency divider 112. At this point in time, the reset signal to the binary counter components is removed, the transmitter is triggered via gate 132, $\overline{M}$ changes to zero, flip-flop 124 is set and both $\overline{Q}$ output terminals of one shots 116 and 118, respectively, are changed to a zero logic state. Accordingly, one of the input signals to NAND gate 126 is in a zero logic state which as previously indicated, inhibits the initiation of counting in binary counter 48. After a predetermined period of time, nominally 200 nanoseconds, one shot 116 reaches its preset monostable duration permitting the $\overline{Q}$ output to change logic states to a true or high level. At this point in time, both of the input terminals to NAND gate 126 are in a true or high state and counter 48 is no longer inhibited because the other terminal receives a one or true state signal from the set Q terminal of flip-flop 124. After an additional period of predetermined delay generally within the range of 4 to 8 microseconds as previously described, one shot 118 also reaches its multivibrator duration at which point $\overline{Q}$ of one shot 118 changes logic states to a high level also changing the state of the AGC gate signal applied to receiver 46. The effects of the logic states of the AGC gate and $\overline{M}$ signals on the receiver, are discussed below in conjunction with FIG. 7.

Thus, when the two millisecond pulse starting the measurement cycle is applied to the input of one shot 118, a negative pulse is applied to the set terminal of flip-flop 124 setting that flip-flop. In addition, a trigger signal is applied through NAND gate 132 to the transmitter to initiate pulse transmission into bolt 12. As soon as the one shot 116 delay expires, both input terminals to NAND gate 126 have ones or true signals applied thereto thus enabling NOR gate 128 to pass the 100 MHz. frequency signal to the clock terminal of high speed flip-flop 80 to commence counting by binary counter 48. The Q output of flip-flop 124 is applied to the receiver, which will be discussed hereinafter in more detail in conjunction with FIG. 7, to enable normal receiver operation subsequent to the transmission of a trigger pulse. The output $\overline{Q}$ of one shot 118 is also applied to the receiver as an AGC gate signal delayed by the preselected time delay of one shot 118 which as previously indicated, is typically within the range of 4 to 8 microseconds. One shot 118 delays the response of the receiver until after all the ringing caused by the transmitted pulse is likely to have dissipated.

Binary counter 48 is enabled to accept the 100 MHz. frequency output of oscillator 50 via NOR gate 128 until one of the two input signals to NAND gate 126 returns to a zero state. This occurs when a stop counting signal is received from the receiver, inverted through NOR gate 122, and applied to the clock terminal of flip-flop 124. Because the D terminal of flip-flop 124 is grounded, the application of a clock signal to flip-flop 124 forces the Q output of that flip-flop to go to a zero state. The output of NAND gate 126 is forced into a one state, thus preventing the clock input to high speed flip-flop 80 from changing during the remainder of that cycle. Therefore, the output of counter 48 remains fixed and the count represents the total time elapsed between the trigger pulse delayed by the period of one shot 116 and the subsequent stop counting signal which is generated by the receiver in response to a valid echo pulse as will now be described in conjunction with FIGS. 7a and 7b.

Figure 7A:
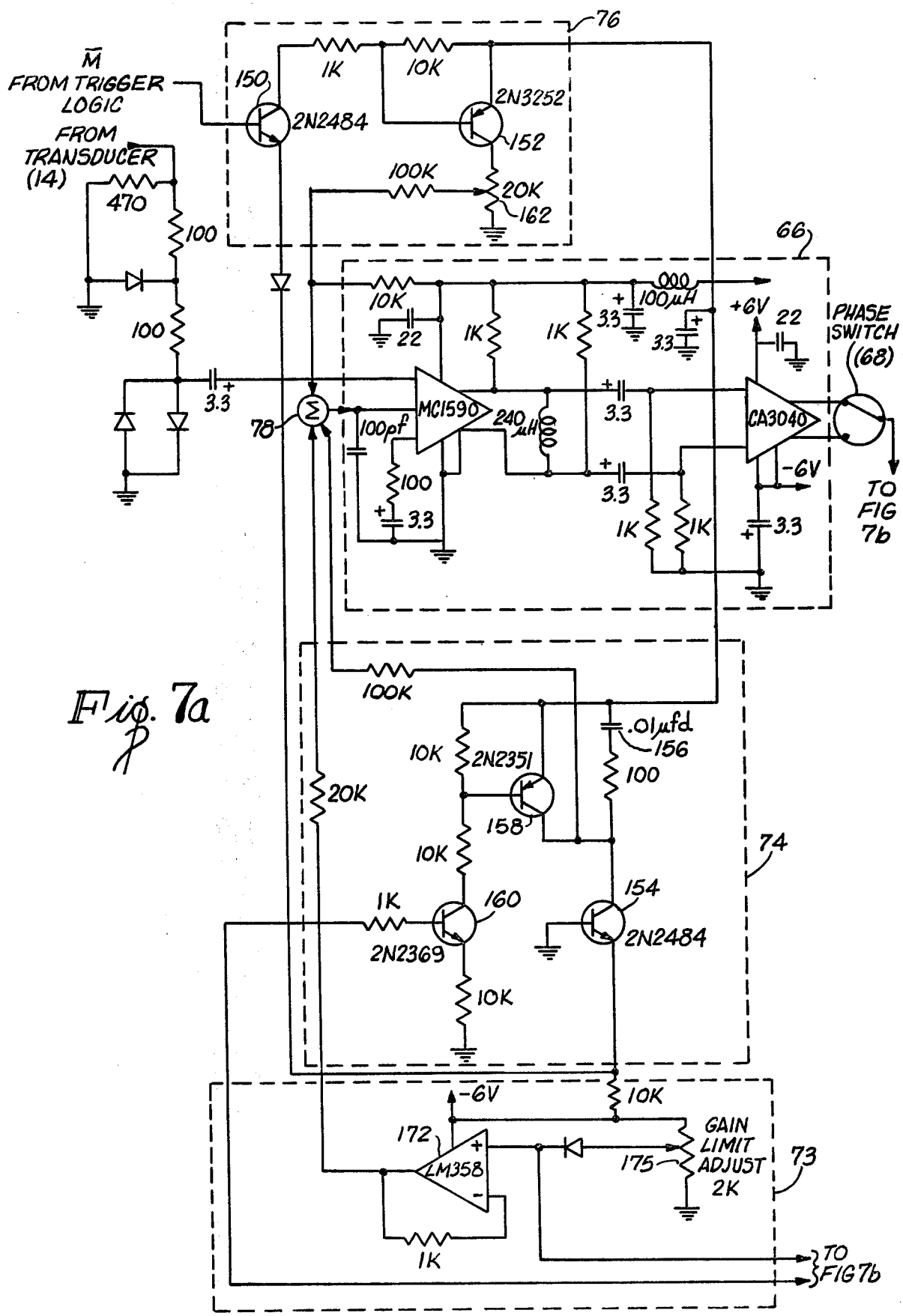

The receiver of the present invention as illustrated in schematic form in FIG. 7, comprising FIGS. 7a and 7b, is divided into dotted line blocks which represent the equivalent blocks of FIG. 4 discussed previously. More specifically, in FIG. 7a there is shown RF amplifier 66, phase switch 68, AGC buffer 73, ramp generator 74, gain dump circuit 76, and gain control junction 78. FIG. 7b includes the schematic representation of echo sense circuit 70 and AGC circuit 72.

RF amplifier 66 is in the embodiment illustrated herein a two stage, 5 MHz., 70 dB amplifier. The amplifier has two stages including a first stage wide band amplifier with AGC, such as a Motorola model MC1590RF/IF amplifier; and a second stage comprising a wideband amplifier such as an RCA model CA3040 wideband amplifier chip. The first stage provides up to 60 dB of AGC range which is controlled by the signal input from junction 78. The signal at junction 78 is a combination of the signals applied from AGC circuit 72 and AGC buffer 73, ramp generator 74, and gain dump circuit 76. RF amplifier 66 has a nominal center frequency of 5 MHz. and a 10 MHz. bandwidth with the output thereof provided at the second stage of the amplifier in a selectable phasing arrangement determined in accordance with the position of phase switch 68 as shown in the right-most portion of FIG. 7a. The signal input to the first stage of RF amplifier 66 is derived from transducer 14 which is connected to the input of the first stage of the amplifier by a suitable matching network which also includes diode protection to isolate the receiver from the high voltage pulse transmitter (not shown).

At the beginning of a measurement cycle, trigger logic circuit 58 transmits an M signal to gain dump circuit 76 and after the receiver delay of one shot 118 is complete it transmits an AGC gate signal to AGC circuit 72. While binary counter 48 is counting as a result of the setting of flip-flop 124 in FIG. 6, the M signal applied to gain dump circuit 76 is in a zero state, thus applying a zero voltage to the base of transistor 150 keeping that transistor in an off state. As a result, transistor 154 in a ramp generator circuit 74 has its emitter connected to a −6 volt supply voltage through a 10K resistor in AGC buffer 73 and capacitor 156 is free to discharge toward that negative voltage. The result is a substantially linear negative going ramp that increases the gain of the first stage of the RF amplifier 66 as long as transistors 158 and 160 in the ramp generator circuit 174 remain in an off state. Those two transistors remain in an off state as long as the $\overline{AGC}$ gate signal derived from trigger logic 58 remains in a zero state and the $\overline{M}$ signal is zero prior to receiving a return echo from the bolt.

When transistor 150 in square wave generator 76 is off transistor 152 is also biased off and the voltage derived at potentiometer 162 is in the collector circuit of transistor 152 is at a ground level which corresponds to maximum gain for the first stage of RH amplifier 66.

The $\overline{AGC}$ gate signal turns on transistor 164 in AGC gate circuit 72 of FIG. 7b, thereby enabling the differential amplifier formed by transistors 166 and 168. The output of the differential amplifier is at the collector of transistor 166 and represents the difference in voltage between the video signal applied to the base of transistor 168 and a variable voltage reference signal applied to the base of transistor 166. The output of the differential amplifier is applied to a driver transistor 170, the output of which is connected to the positive input terminal of operational amplifier 172 shown in FIG. 7a. The output of operational amplifier 172 is applied to junction 78 along with the ramp signal derived from ramp generator circuit 74 and the stepped signal derived from square wave circuit 76. A gain limit adjustment potentiometer 175 is provided at the positive input to amplifier 172 to limit the AGC excursion as desired.

When the stop counting signal is generated by echo sense circuit 70 in response to a received valid echo pulse, the $\overline{M}$ signal from trigger logic circuit 58 is changed to a positive voltage turning on transistor 150 and transistor 152. As a result, the voltage at potentiometer 162 suddenly increases through transistor 152 whereby the gain is stepped down to preclude the reception of subsequent echo pulses. In addition, transistor 154 is turned off thereby isolating ramp generator circuit 74 from the −6 volts supply, terminating the ramp at the voltage reached at the occurence of $\overline{M}$. It is to be noted that the output of transistor 170 in the AGC gate circuit 72 of FIG. 7b is also connected to an RC circuit comprising capacitor 174 and 1 MegOhm resistor 176 which is in turn connected to the −6 volts supply voltage. This RC circuit acts as a fast attack, slow decay network for the AGC circuit wherein capacitor 174 is rapidly charged during the application of the video signal to the base of transistor 168 and slowly discharged in the absence of a signal.

Echo sense circuit 70, shown in the upper portion of FIG. 7b, is connected to the output of phase switch 68 discussed previously in conjunction with FIG. 7a and comprises primarily an operational amplifier comparator 180 such as a Fairchild model 760. With no received signal present at the input terminal 2 of comparator 180, the output of the comparator at pin 6 is in a low state at ground level and the feedback output at pin 7 is in a high state of approximately 3 volts. Consequently, variable resistor 181 provides a small adjustable positive voltage reference to pin 3 of the comparator. This reference voltage is adjustable to provide variations in threshold to which comparator 180 responds for optimizing the probability of responding only to the first valid echo signal received. When the amplified signal applied to terminal 2 of comparator 180 exceeds the threshold signal applied to terminal 3, the signal at output terminal 6 suddenly goes to a positive level and the feedback signal from terminal 7 goes to a zero level. As a result, the comparator reference feedback voltage then goes to zero so that the output at terminal 6 will immediately revert back to zero volts upon the occurence of the first zero crossing after the threshold is exceeded.

Thus, during each transmitted pulse cycle, the first received reflected pulse that includes a voltage swing above a pre-established threshold produces a positive pulse at the next zero crossing, which pulse is the stop counting signal. That signal is applied to the trigger logic of FIG. 6 where the signal is inverted by NOR gate 122 before being applied to the clock terminal of flip-flop 124. It is the positive going edge of the inverted pulse at the clock terminal of flip-flop 124 which corresponds in timing to the zero crossing of the received signal after it first exceeds the threshold that clocks the flip-flop. Thereafter, the 100 MHz. oscillator pulses are prevented from reaching the binary counter for the remainder of that cycle as discussed previously.

Reference will now be made to FIG. 8 which comprises nine signal waveforms of various signals previously discussed in conjunction with FIGS. 6 and 7, to enhance the understanding of the present invention. Waveform a is the 2 millisecond period squarewave generated at the Q12 terminal of frequency divider 112 of FIG. 6. This 2 millisecond period is the basic measurement cycle of the apparatus. Waveform b is the one millisecond period squarewave available at terminal Q11 of frequency divider 112 of FIG. 6 and is used primarily to provide resetting functions 75% through the measurement cycle, that is, 1.5 millisecond after the occurence of the transmitted pulse. Waveform c is the C-gate signal generated at the Q terminal of receiver delay one shot 118 of FIG. 6 and that is used primarily to control the initiation of the AGC gate signal to the receiver to prevent the ringing effects of the transmitted pulse from interfering with the measurement process. As previously indicated, C-gate signal pulse diration is typically in the range of 4–8 microseconds but is adjustable to provide an optimum value for the measurement taking place. Waveform d is the $\overline{AGC}$ gate signal applied to the AGC gate circuit 72 (as shown in FIG. 7b) by the trigger logic 58 (shown in FIG. 6) to enable the gain circuits of receiver 46. The AGC gate signal, which permits normal receiver operation when it is in a low state, does not begin to make the transition to that low state until the termination of the C-gate signal of waveform c. It is then reset upon the termination of the 1 millisecond reset cycle established by the 1 kiloHertz signal of waveform b.

Waveform e of FIG. 8 is the zero delay signal produced at the Q terminal of counter delay one shot 116 of FIG. 6. As previously indicated, the timed output of one shot 116 is also adjustable but is typically 200 nanoseconds in duration and is used to compensate for the time delay between the pulse trigger provided by trigger logic 58 and the entry of the transmitted pulse into the bolt 12. The effect of the zero adjust time delay of waveform e is seen in waveform f which is an inverted representation of the output of NAND gate 126 of FIG. 6. Therefore, waveform f represents the time period over which the binary counter 48 is allowed to count the output of 100 MHz. oscillator 50. In the particular example illustrated in the waveforms of FIG. 8, the counter would begin counting immediately upon the termination of the zero adjust pulse of waveform e and continue counting until the received echo pulse first accomplishes a zero crossing subsequent to exceeding the selected threshold as indicated by the video representation of the transducer pulses in waveform g.

In waveform g of FIG. 8 the first signal indication beginning at the initiation of the measurement cycle is the transmitted pulse $t_p$ and the second signal representation is the received echo pulse $r_p$. The additional signal representations following $r_p$ represent further received echo signals which are ignored by the receiver of the present invention. Waveform h represents the gain characteristic of receiver 46. Just prior to the transmission of transmitter pulse $t_p$, the gain of receiver 46 is substantially fixed at a value determined by the previous signal history of the AGC circuit as is well-known in the art. However, immediately upon the transmission of pulse $t_p$ into bolt 12, the gain ramp is activated and the gain increases linearly to either a maximum value, if no signal is received, or until the received signal meets the threshold and zero crossing criteria for the echo sense circuit 70 of receiver 46. When this event occurs, the gain dump circuit is activated and the gain of the receiver makes a substantially instantaneous negative change which prevents the receiver from receiving subsequent invalid echo signals which may also exceed the threshold value. The entire gain circuit is then reset at the 1 millisecond reset time as previously indicated.

The last waveform of FIG. 8, that is waveform i, represents the count termination signal applied to the clock terminal of flip-flop 124 of FIG. 6. This is the stop counting signal from the receiver inverted by NOR gate 122 of FIG. 6. Flip-flop 124 of FIG. 6 responds to the first positive going edge of the count termination signal of waveform i resulting from the output of echo sense circuit 70 of FIG. 7b. In the example of the count termination signal of waveform i as shown in FIG. 8, two sequential pulses are shown to indicate the effects of the second traversal of the waveform of received pulse $r_p$ beyond the threshold level and then to zero. However, only the first positive going transition of the count termination signal of waveform i effects a change in the output state of flip-flop 124 of FIG. 6. Therefore, the second such sequential pulse waveform i is ignored by the present invention.

The program stored in EPROM 98 for carrying out the operation of the present invention is disclosed in total in Table I attached hereto as an appendix. Table I includes three columns, namely, an address column, an opcode column and a remarks column. The address column lists a three digit hexadecimal representation of each of the 8 bit address locations in EPROM 98. The opcode column lists a two digit hexadecimal representation of the 8 bits of binary code stored at each such location and the remarks column briefly indicates the nature of the operation being carried out in the program in response to a particular opcode or sequential plurality of opcodes. Those having skill in the art to which the present invention pertains will find the bolt gauge program listed in Table I to be a complete and precise description of each step carried out by the program of the present invention. Accordingly, for purposes of clarity and brevity, only the major computational operations carried out by the program shall now be described in general terms.

More specifically, the output of counters 84, 86 and 88 available at input/output ports 52a, 52b and 52c, respectively, are input to an accumulator in microprocessor 94. This process is repeated 160 times sequentially as long as any one pulse count does not differ from the prior pulse count by more than a count of 8. The program thus acts with the counters to provide a form of digital filtering which prevents inaccuracies due to anomalies in the count that would be represented by a sudden change in the count by a predetermined number. In the preferred embodiment this number is 8 but of course it will be understood that the program is readily changed to utilize any desired count change criteria.

If the count change limit is exceeded, the process of loading the accumulator is restarted. On the other hand, if the count change limit is not exceeded, the process of loading the accumulator with 160 successive counts is completed and the program next divides the accumulator output by 4 and adds the quotient to the original contents of the accumulator. This is the equivalent of multiplying the accumulator contents by a factor of 1.25. This factor is used to compensate for the selected frequency of oscillator 50 which would ideally be an oscillator having a frequency of 125 MHz. However, in the preferred embodiment of the invention in order to be assured of proper component performance despite frequency limitations thereof, the lower frequency of 100 MHz. is used and compensation therefore is accomplished in the computer portion of the invention as just described. Of course it will be clear that the program is readily changed to multiply the contents of the accumulator in this step by any factor dependent upon the selected frequency of oscillator 50.

The program next divides the contents of the accumulator by a factor of 4 which converts the accumulator contents to the appropriate units level for measurement time that may be used in the remainder of the computation. Next the computer inputs the material velocity factor set in thumbwheel switch 38 shown in FIG. 2. Because the thumbwheel switches provide a binary coded decimal output, the computer then converts material velocity in BCD to a binary format. Next the binary representation of material velocity is multiplied by the contents of the accumulator and that produce represents the uncompensated reading of the length of the bolt under test. The computer next inputs the temperature reading input into thumbwheel switch 28 and converts that representation to binary format. It then subtracts 25 degrees from the input temperature to provide a difference temperature including a sign bit indicating whether the input temperature is above or below the reference temperature of 25 degrees C. Next the temperature factor thumbwheel switch 34 is input to the computer and converted to binary format. Then the temperature factor is multiplied by the temperature difference and the results are either added or subtracted from 1 depending upon the polarity of the temperature sign bit. Next the result of the addition or subtraction from 1 in the previous step is multiplied by the uncompensated reading of the bolt length. The result is a compensated reading of bolt length which is more accurate because it takes the effects of temperature into account.

If stretch/length switch 30 has been set to the length position, indicating that the current measurement is of an unstretched bolt, the compensated reading obtained in the previous step is converted to a binary coded decimal representation and applied to the display 20 to provide the user with an indication of the unstressed bolt length compensated for temperature. On the other hand, if the stretch/length switch 30 is set to the stretch position, indicating that the bolt being measured is under stress, the computer program continues with the following steps:

The material factor set into thumbwheel switch 36 is input and converted to binary. Then the initial length is set into thumbwheel switch 26 and corresponding to a prior unstressed bolt length measurement is also input and converted to binary. The program then subtracts the initial length from the compensated reading and multiplies that difference by the material factor. The results are then converted to binary coded decimal format and applied to display 20 to provide an indication of the change in length of the bolt subjected to stress as compared to its initial length and compensated for both temperature and the effects of the stress on the velocity of the acoustic energy through the bolt. A shorthand representation of the program operation as just described is indicated below in equations 1 and 2, the former corresponding to the compensated reading of an unstressed bolt and the latter corresponding to the stretch reading of a stressed bolt.

$$READING_{COMP} = READING_{UNCOMP} [1+(TEMP\ FACTOR)(TEMP-25°\ C.)] \quad (1)$$

$$\Delta READING = (MATERIAL\ CORRECT\ FACTOR)\ ]READING_{COMP} - INIT\ LGTH] \quad (2)$$

It will now be understood that what has been disclosed herein is an apparatus and process for measuring the length of unstressed and stressed bolts to extreme accuracies and including means for inclusion of correction factors depending the stress conditon of the bolt, the temperature in which the measurement is made and the thermal correction coefficient of the material under test. The invention thus provides a length or length difference measurement which is based upon an accurate representation of the actual velocity of acoustical energy in the stressed bolt being tested. The apparatus utilizes a microprocessor-based digital system including a binary counter which is connected to an extremely high frequency oscillator. The counter is adapted to provide a high resolution count depending upon the time interval between a first pulse entering the outer surface of the bolt under test at the probe input end, and a second pulse which is derived from the reflection return of the ultrasonic energy from the opposite end of the bolt. A number of thumbwheel switches are provided which permit input of variables corresponding to material velocity, stress correction factor, measurement temperature and thermal correction coefficient. In addition, a switch is provided for selecting digital display of either full bolt length or the difference between full elongation and initial length. The latter may be entered via an additional thumbwheel switch after it has been measured by means of the invention or after it has been copied from tabulated data. The invention utilizes a unique digital filtering algorithm to ensure accurate and stable measurements. Also utilized is a novel receiver circuit which is designed to overcome the unique acoustical characteristics of threaded bolts by means of a dual characteristic echo sensing circuit used to ensure measurement accuracy despite acoustic pulse distortion. The receiver also includes a special gain contour circuit to further ensure measurement accuracy despite spurious echoes that commonly arise in the acoustic measurement in threaded bolts.

Those having skill in the art to which the present invention pertains will understand that the present invention provides a unique method and apparaus for measuring the elongation of stress bolts in situ including means for entering data representative of nominal length, nominal acoustic velocity, acoustic velocity stress correction factor, temperature of the measurement and thermal expansion coefficient to provide a highly accurate digital representation of bolt elongation. Although a preferred embodiment of the apparatus of the invention has been disclosed herein, it will now be apparent that numerous modifications may be made to the invention without deviating from the scope of protection. For example, although the preferred embodiment provides a microprocessor-based portable electronic instrument for measuring the elongation of stressed bolts, it will be understood that it is possible to carry out such measurements and computations utilizing other digital devices as well as analog circuits. Furthermore, it will be understood that although a preferred receiver circuit has been disclosed, which circuit reduces the difficulty of carrying out the measurement process by decreasing the effects of certain acoustical anomalies commonly encountered in measuring the length of threaded bolts by acoustic measurement means, the process of the present invention may be readily carried out by using more common receivers as well as receivers which employ other types of circuits for decreasing the effects of such anomalies. Thus, it will be understood that all such modifications and additions are currently contemplated as being within the scope of the present invention which is to be limited only by the claims appended hereto.

TABLE I

BOLT GAGE PROGRAM

| ADDRESS | OP CODE | REMARKS |
| --- | --- | --- |
| 000 | C4 | NO OPERATION |
| 001 | C0 | GO TO 653 TO INITIALIZE DISPLAY |
| 002 | 06 | |
| 003 | 53 | |
| 004 | F8 | SET HI R1=07 POINTER FOR MULTIPLY SUBROUTINE |
| 005 | 07 | |
| 006 | B1 | |
| 007 | E0 | SET RX=0 |
| 008 | F8 | |
| 009 | 08 | SET HI R8 AND R9=08 RAM POINTER |
| 00A | B8 | |
| 00B | B9 | |
| 00C | F8 | SET HI R7=0 MINUS SIGN FLAG |
| 00D | 00 | |
| 00E | B7 | |
| 00F | F8 | SET LO R5=OF |
| 010 | OF | |
| 011 | A5 | |
| 012 | F8 | SET HI R2=04 POINTER FOR BCD SUBROUTINE |
| 013 | 04 | |
| 014 | B2 | |
| 015 | 35 | BRANCH IF BATTERY OK TO 01C |
| 016 | 1C | |
| 017 | 64 | TURN ON COLON (BATTERY LOW) |
| 018 | B8 | |
| 019 | 6F | |
| 01A | 30 | BRANCH TO 01F |
| 01B | 1F | |
| 01C | 64 | TURN OFF COLON (BATTERY OK) |
| 01D | BF | |
| 01E | 6F | TURN OFF COLON (BATTERY OK) |
| 01F | E9 | SET RX=9 |
| 020 | F8 | SET LO R9=OF |
| 021 | OF | |
| 022 | A9 | |
| 023 | 7B | SET Q=1 |
| 024 | F8 | SET LOOP COUNTER=8 LO R6 |
| 025 | 08 | |
| 026 | A6 | |
| 027 | F8 | SET D REGISTER EQUAL TO 0 |
| 028 | 00 | |

TABLE I-continued
BOLT GAGE PROGRAM

| ADDRESS | OP CODE | REMARKS |
|---|---|---|
| 029 | 73 | STORE D, X−1 |
| 02A | 26 | DECREMENT LO R6 |
| 02B | 86 | R6→D |
| 02C | 3A | BRANCH IF D DOESN'T EQUAL O TO 027 |
| 02D | 27 | |
| 02E | F8 | SET LO R6 = 128 |
| 02F | 80 | LONG BOLT MEASUREMENT |
| 030 | A6 | |
| 031 | 37 | BRANCH IF SW EQUALS LONG BOLT MEASUREMENT TO 03D |
| 032 | 3D | |
| 033 | F8 | |
| 034 | A0 | SET LO R6 = 160 |
| 035 | A6 | SHORT BOLT MEASUREMENT |
| 036 | 30 | BRANCH TO 03D |
| 037 | 3D | |
| 038 | | |
| 039 | | SPARE |
| 03A | | |
| 03B | | |
| 03C | | SPARE |
| 03D | F8 | |
| 03E | 06 | SET LO R9 = 06 |
| 03F | A9 | |
| 040 | 34 | LOOP UNTIL INPUT GOES HIGH |
| 041 | 40 | |
| 042 | 3C | LOOP UNTIL INPUT GOES LOW |
| 043 | 42 | |
| 044 | C0 | |
| 045 | 01 | BRANCH TO 180 |
| 046 | 80 | |
| 047 | | |
| 048 | | SPARE |
| 049 | | |
| 04A | | |
| 04B | | |
| 04C | F8 | |
| 04D | 00 | SET LO RC = 00 |
| 04E | AC | |
| 04F | F8 | SET LO R9 TO A9 |
| 050 | 0E | ACCUMULATOR LSB+1 |
| 051 | A9 | |
| 052 | 8F | LO RF INTO D − ACCUMULATOR |
| 053 | F4 | ADD TO 80E |
| 054 | AF | D INTO LO RF |
| 055 | 73 | STORE, RX − 1 |
| 056 | 8E | LO RE INTO D − ACCUMULATOR |
| 057 | 74 | ADD TO 80D + CARRY |
| 058 | AE | SAVE IN LO RE |
| 059 | 73 | STORE, X−1 |
| 05A | 8D | LO RD INTO D − ACCUMULATOR |
| 05B | 74 | ADD TO 80C + CARRY |
| 05C | AD | SAVE IN LO RD |
| 05D | 73 | STORE, RX−1 |
| 05E | 8C | LO RC INTO D − ACCUMULATOR |
| 05F | 74 | ADD TO 80B + CARRY |
| 060 | AC | SAVE IN LO RC |
| 061 | 73 | STORE, RX−1 |
| 062 | 26 | DEC. LO R6 − #SAMPLES COUNTER |
| 063 | 86 | LO R6 INTO D − ACCUMULATOR |
| 064 | 3A | BRANCH IF D IS NOT O TO 03D |
| 065 | 3D | |
| 066 | F8 | |
| 067 | EC | SET LO R1 = EC |
| 068 | A1 | |
| 069 | D1 | GO TO RIGHT SHIFT |

TABLE I-continued
BOLT GAGE PROGRAM

| ADDRESS | OP CODE | REMARKS |
|---|---|---|
| | | SUBROUTINE |
| 06A | F8 | |
| 06B | EC | SET LO R1 = EC |
| 06C | A1 | |
| 06D | D1 | GO TO RIGHT SHIFT SUBROUTINE |
| 06E | F8 | SET LO R9 = 0E (ACCUMULATOR LSB) |
| 06F | 0E | |
| 070 | A9 | |
| 071 | 8F | LO RF INTO D |
| 072 | F4 | ADD TO 80E |
| 073 | 73 | STORE, X−1 |
| 074 | 8E | LO RE INTO D |
| 075 | 74 | ADD TO 80D + CARRY |
| 076 | 73 | STORE, X−1 |
| 077 | 8D | LO RD INTO D |
| 078 | 74 | ADD TO 80C + CARRY |
| 079 | 73 | STORE, X−1 |
| 07A | 8C | LO RC INTO D |
| 07B | 74 | ADD TO 80B + CARRY |
| 07C | 73 | STORE, X−1 |
| 07D | F8 | |
| 07E | 05 | SET LO R6=05 |
| 07F | A6 | |
| 080 | 37 | BRANCH IF SW EQUALS LONG BOLT MEASUREMENT TO 086 |
| 081 | 86 | |
| 082 | F8 | |
| 083 | 02 | SET LO R6=02 |
| 084 | A6 | |
| 085 | C4 | NO OPERATION |
| 086 | F8 | |
| 087 | EC | SET LO R1=EC |
| 088 | A1 | |
| 089 | D1 | GO TO RIGHT SHIFT SUBROUTINE |
| 08A | 26 | DEC. LO R6 |
| 08B | 86 | LO R6 INTO D |
| 08C | 3A | BRANCH IF D DOESN'T EQUAL 0 |
| 08D | 86 | |
| 08E | F8 | |
| 08F | 0B | SET LO R9=0B |
| 090 | A9 | |
| 091 | F8 | SET LO R8=14 |
| 092 | 14 | SET LO R8=14 |
| 093 | A8 | |
| 094 | 72 | LOAD 80B,X+1 |
| 095 | 58 | STORE AT 814 |
| 096 | 18 | INCREMENT R8 |
| 097 | 72 | LOAD 80C, X+1 |
| 098 | 58 | STORE AT 815 |
| 099 | 18 | INCREMENT R8 |
| 09A | 72 | LOAD 80D, X+1 |
| 09B | 58 | STORE AT 816 |
| 09C | 18 | INCREMENT R8 |
| 09D | 72 | LOAD 80E, X+1 |
| 09E | 58 | STORE AT 817 |
| 09F | 18 | INCREMENT R8 |
| 0A0 | 7B | SET Q EQUAL 1 |
| 0A1 | E0 | RX=0 |
| 0A2 | 65 | SET CONTROL EQUAL 01 LSB BYTE |
| 0A3 | 01 | |
| 0A4 | E9 | RX=9 |
| 0A5 | 6D | LOAD DATA |
| 0A6 | FB | INVERT DATA |
| 0A7 | FF | |
| 0A8 | AE | STORE IN LO RE |

TABLE I-continued
BOLT GAGE PROGRAM

| ADDRESS | OP CODE | REMARKS |
|---|---|---|
| 0A9 | FA | MASK OFF FIRST 4 BITS |
| 0AA | 0F | |
| 0AB | AF | STORE IN LO RE |
| 0AC | 8E | LOAD LO RE |
| 0AD | F6 | RIGHT SHIFT 3 TIMES |
| 0AE | F6 | |
| 0AF | F6 | |
| 0B0 | F6 | RIGHT SHIFT 1 TIME |
| 0B1 | AE | STORE IN LO RE |
| 0B2 | E0 | RX=0 |
| 0B3 | 65 | SET CONTROL EQUAL 02 LSB+1 BYTE |
| 0B4 | 02 | |
| 0B5 | E9 | RX=9 |
| 0B6 | 6D | LOAD DATA |
| 0B7 | FB | INVERT DATA |
| 0B8 | FF | |
| 0B9 | AC | STORE IN LO RC |
| 0BA | FA | MASK OFF FIRST 4 BITS |
| 0BB | 0F | |
| 0BC | AD | STORE IN LO RD |
| 0BD | 8C | LOAD LO RC |
| 0BE | F6 | RIGHT SHIFT 4 TIMES |
| 0BF | F6 | |
| 0C0 | F6 | |
| 0C1 | F6 | |
| 0C2 | AC | STORE IN LO RC |
| 0C3 | E0 | RX=0 |
| 0C4 | 65 | SET CONTROL EQUAL 04 MSB BYTE |
| 0C5 | 04 | |
| 0C6 | E9 | RX=9 |
| 0C7 | 6D | LOAD DATA |
| 0C8 | FB | INVERT |
| 0C9 | FF | |
| 0CA | AA | STORE IN LO RA |
| 0CB | FA | MASK OFF FIRST 4 BITS |
| 0CC | 0F | |
| 0CD | AB | STORE IN LO RB |
| 0CE | 8A | LOAD TO RA |
| 0CF | F6 | RIGHT SHIFT 4 TIMES |
| 0D0 | F6 | |
| 0D1 | F6 | |
| 0D2 | F6 | |
| 0D3 | AA | STORE IN LO RA |
| 0D4 | F8 | SET LO R2=00 |
| 0D5 | 00 | |
| 0D6 | A2 | |
| 0D7 | D2 | BRANCH TO BCD TO BINARY FRACTION CONVERSION SUBROUTINE |
| 0D8 | F8 | SET LO R2=00 |
| 0D9 | 0D | |
| 0DA | A9 | |
| 0DB | 72 | LOAD 80D,X+1 |
| 0DC | A5 | ACCUMULATOR INTO LO R5 |
| 0DD | 72 | LOAD 80E, X+1 |
| 0DE | A4 | ACCUMULATOR INTO LO R4 |
| 0DF | 72 | LOAD 80F, X+1 |
| 0E0 | A3 | ACCUMULATOR INTO LO R3 |
| 0E1 | F8 | SET LO R6=00 |
| 0E2 | 00 | |
| 0E3 | A6 | |
| 0E4 | F8 | SET LO R1=80 |
| 0E5 | 80 | |
| 0E6 | A1 | |
| 0E7 | D1 | GO TO MULTIPLY SUBROUTINE |
| 0E8 | F8 | SET LO R9=0A |
| 0E9 | 0A | |
| 0EA | A9 | SET LO R9=0A |
| 0EB | 72 | LOAD 80A, X+1 |
| 0EC | BA | STORE IN HI RA (MSB) |
| 0ED | 72 | LOAD 80B, X+1 |
| 0EE | BB | STORE IN HI RB (LSB+1) |
| 0EF | 72 | LOAD 80C, X+1 |
| 0F0 | BC | STORE IN HI RC (LSB) |
| 0F1 | C0 | GO TO 100 |
| 0F2 | 01 | |
| 0F3 | 00 | |
| 0F4 | | |
| 0F5 | | |
| 0F6 | | |
| 0F7 | | |
| 0F8 | | |
| 0F9 | | SPARE |
| 0FA | | |
| 0FB | | |
| 0FC | | |
| 0FD | | |
| 0FE | | |
| 0FF | | |
| 100 | F8 | SET R9 .0=02 |
| 101 | 02 | |
| 102 | A9 | |
| 103 | 7B | SET Q=1 |
| 104 | E0 | SET X=0 |
| 105 | 65 | OUTPUT 08 TO Z16 TO ENABLE TEMP. |
| 106 | 08 | |
| 107 | E9 | SET X=9 |
| 108 | 6D | INPUT TEMP. D+M(0802) |
| 109 | FB | INVERT DATA |
| 10A | FF | |
| 10B | AF | PUT IN RF.0 |
| 10C | FA | MASK 4 MUST SIG. BITS |
| 10D | 0F | |
| 10E | 59 | STORE VIA M(0802) |
| 10F | 8F | GET RF.0 |
| 110 | F6 | SHIFT RIGHT 4 TIMES |
| 111 | F6 | |
| 112 | F6 | |
| 113 | F6 | |
| 114 | AF | STORE IN RF.0 |
| 115 | 8F | GET RF.0 |
| 116 | 32 | IF D=0, BRANCH TO 1F |
| 117 | 1F | |
| 118 | 2F | DECREMENT REG F |
| 119 | F8 | ADD 0A TO MEMORY→D |
| 11A | 0A | |
| 11B | F4 | |
| 11C | 59 | STORE RESULTS IN M(0802) |
| 11D | 30 | BRANCH TO 15 |
| 11E | 15 | |
| 11F | 09 | LOAD VIA 9 M(0801) PUT IN LOW REG.F (BINARY CONVERTED TEMP.) |
| 120 | AF | |
| 121 | 6B | |
| 122 | FA | MASK ALL BUT TEMP. SIGN(MSB) |
| 123 | 80 | |
| 124 | 32 | IF D=0, GO TO 3B (NEG. SIGN) |
| 125 | 3B | IF D=0, GO TO 3B(NEG.SIGN) |
| 126 | 8F | GET LO RF |

TABLE I-continued
BOLT GAGE PROGRAM

| ADDRESS | OP CODE | REMARKS |
|---|---|---|
| 127 | FF | TEMP. INPUT - 25° C. |
| 128 | 19 | |
| 129 | 3B | BRANCH TO 3 IF DF=O (NEG.DIFF.) |
| 12A | 31 | |
| 12B | BF | PUT IN RF.1 |
| 12C | F8 | LOAD OO INTO RE.1 |
| 12D | OO | |
| 12E | BE | |
| 12F | 30 | BRANCH TO 38 |
| 130 | 38 | |
| 131 | 8F | GET LO REG. F |
| 132 | FD | SUBTRACT(19−RF.O) TEMP. IN<25° C. |
| 133 | 19 | |
| 134 | BF | PUT D IN RF.1 |
| 135 | F8 | LOAD 80 INTO RE.1 |
| 136 | 80 | |
| 137 | BE | |
| 138 | CO | LONG BRANCH 0200 |
| 139 | O2 | |
| 13A | OO | |
| 13B | 8F | GET RF.O |
| 13C | FC | ADD 19 TO TEMP. INPUT #DEGREES BELOW REF. TEMP. |
| 13D | 19 | |
| 13E | 30 | BRANCH TO 34 |
| 13F | 34 | |
| 140 | | SPARES |
| 141 | | |
| 142 | | |
| 143 | | SPARES |
| 144 | | |
| 145 | | |
| 146 | | |
| 147 | | |
| 148 | | |
| 149 | | |
| 14A | | |
| 14B | | |
| 14C | | |
| 14D | | SPARES |
| 14E | | |
| 14F | | |
| 150 | | |
| 151 | | |
| 152 | | |
| 153 | | |
| 154 | | |
| 155 | | |
| 156 | | |
| 157 | | SPARES |
| 158 | | |
| 159 | | |
| 15A | | |
| 15B | | |
| 15C | | |
| 15D | | |
| 15E | | |
| 15F | | |
| 160 | | |
| 161 | | SPARES |
| 162 | | |
| 163 | | |
| 164 | | |
| 165 | | |
| 166 | | |
| 167 | | |
| 168 | | |
| 169 | | |
| 16A | | |
| 16B | | SPARES |
| 16C | | |
| 16D | | |
| 16E | | |
| 16F | | |
| 170 | | |
| 171 | | |
| 172 | | |
| 173 | | |
| 174 | | |
| 175 | | SPARES |
| 176 | | |
| 177 | | |
| 178 | | |
| 179 | | |
| 17A | | |
| 17B | | |
| 17C | | |
| 17D | | |
| 17E | | |
| 17F | | SPARE |
| 180 | 6B | INPUT HIGH ORDER BITS PLUS STATUS (STORE IN (0806) |
| 181 | FA | AND IMMEDIATE |
| 182 | 01 | AND O1 WITH D REGISTER |
| 183 | 32 | SHORT BRANCH IF 17TH BIT = 0 TO 8D |
| 184 | 8D | |
| 185 | 6A | INPUT BITS 8-15 INTO (0806) (RAM) |
| 186 | FA | AND BITS (8-15) WITH 80 (1000 0000) |
| 187 | 80 | |
| 188 | 32 | SHORT BRANCH IF 15TH BIT = O TO 8D |
| 189 | 8D | |
| 18A | 30 | SHORT BRANCH TO CO |
| 18B | CO | |
| 18C | | |
| 18D | 69 | INPUT BITS 0-7 INTO D & STORE (0806) (X=9) |
| 18E | AF | BITS 0-7 IN REG. F LOW |
| 18F | 29 | DECREMENT REG 9 (0805) |
| 190 | 6A | LOAD BITS 8-15 INTO D &(0805) |
| 191 | AE | PUT BITS 8-15 IN REG.E LOW |
| 192 | 29 | DECREMENT REG. 9 (0804) |
| 193 | 6B | INPUT BITS 16 THRU 23 INTO D & 0804 |
| 194 | FA | AND D REGISTER WITH 01, MASKING EVERYTHING BUT BIT 16 |
| 195 | 01 | |
| 196 | AD | PUT BIT 16 IN REGISTER D LOW |
| 197 | 59 | STORE BIT 16 IN MEMORY LOCATION 0804 (X=9) |
| 198 | 31 | SHORT BRANCH IF Q=1 TO BO |
| 199 | BO | |

TABLE I-continued
BOLT GAGE PROGRAM

| ADDRESS | OP CODE | REMARKS |
|---|---|---|
| 19A | F8 | LOAD 06 INTO D |
| 19B | 06 | |
| 19C | A9 | PUT IN R9.0 |
| 19D | 9F | GET F.1 (LSB'S + 08) |
| 19E | F7 | SUBTRACT ACCUM.-MEMORY 0806 |
| 19F | FA | AND ACCUM. WITH FO MASKING LOWER 4 BITS |
| 1AO | FO | |
| 1A1 | 3A | BRANCH TO CO IF ACCUM. NOT ZERO |
| 1A2 | CO | |
| 1A3 | 29 | DECREMENT REG 9 (X=9) (R9 = 0805) |
| 1A4 | 9E | GET HIGH REGISTER E (LAST BINARY +08) |
| 1A5 | 77 | CONTINUE SUBTRACTION |
| 1A6 | 29 | DECREMENT R9 |
| 1A7 | 9D | GET HIGH REGISTER D |
| 1A8 | 77 | CONTINUE SUBTRACTION |
| 1A9 | 3B | IF DF=O, GO TO CO |
| 1AA | CO | |
| 1AB | 30 | OTHERWISE GO TO BO |
| 1AC | BO | |
| 1AD | | SPARE |
| 1AE | | |
| 1AF | | |
| 1BO | 8F | GET LOW REG. F.O (BITS 0–7) |
| 1B1 | FC | ADD 08, DF, D |
| 1B2 | 08 | |
| 1B3 | BF | PUT RESULTS IN REG. F HIGH |
| 1B4 | 8E | GET LOW REG. E |
| 1B5 | 7C | ADD OO, D, DF |
| 1B6 | OO | |
| 1B7 | BE | PUT RESULTS IN HI REG. E |
| 1B8 | 8D | GET LOW REG. D |
| 1B9 | 7C | ADD OO, D, DF |
| 1BA | OO | |
| 1BB | BD | PUT RESULTS IN HI REG. D |
| 1BC | 7A | RESET Q |
| 1BD | CO | LONG BRANCH TO 004C |
| 1BE | OO | |
| 1BF | 4C | |
| 1CO | 25 | DECREMENT R5 |
| 1C1 | 85 | GET R5.0 |
| 1C2 | C2 | IF D=O, GO TO 0653 |
| 1C3 | 06 | |
| 1C4 | 53 | |
| 1C5 | EO | SET X=O |
| 1C6 | CO | LONG BRANCH TO 0012 |
| 1C7 | OO | |
| 1C8 | 12 | |
| 1C9 | | SPARE |
| 1CA | | |
| 1CB | | |
| 1CC | | |
| 1CD | | |
| 1CE | | |
| 1CF | | |
| 1DO | | |
| 1D1 | | |
| 1D2 | | SPARE |
| 1D3 | | |
| 1D4 | | |
| 1D5 | | |
| 1D6 | | |
| 1D7 | | |
| 1D8 | | |
| 1D9 | | |
| 1DA | | |
| 1DB | | SPARE |
| 1DC | | |
| 1DD | | |
| 1DE | | |
| 1DF | | |
| 1EO | | |
| 1E1 | | |
| 1E2 | | |
| 1E3 | | |
| 1E4 | | |
| 1E5 | | SPARE |
| 1E6 | | |
| 1E7 | | |
| 1E8 | | |
| 1E9 | | |
| 1EA | | |
| 1EB | | |
| 1EC | | |
| 1ED | | |
| 1EF | | |
| 1FO | | |
| 1F1 | | SPARE |
| 1F2 | | |
| 1F3 | | |
| 1F4 | | |
| 1F5 | | |
| 1F6 | | |
| 1F7 | | |
| 1F8 | | |
| 1F9 | | |
| 1FA | | |
| 1FB | | |
| 1FC | | |
| 1FD | | |
| 1FE | | |
| 1FF | | |
| 200 | 7B | SET Q |
| 201 | EO | SET X=O |
| 202 | 65 | OUTPUT 10 TO Z16 SELECTING EXPANSION CUEFF INPUT |
| 203 | 10 | |
| 204 | E9 | SET X=9 |
| 205 | 6D | INPUT 2 LEAST SIG. DIGITS OF EXP. COEFF. |
| 206 | FB | INVERT DATA |
| 207 | FF | |
| 208 | AE | STORE IN RE.O |
| 209 | FA | MASK 2ND DIGIT |
| 20A | OF | |
| 20B | AF | STORE IN RF.O |
| 20C | 8E | GET ORIGINAL INPUT |
| 20D | F6 | SHIFT RIGHT 1 TIME |
| 20E | F6 | SHIFT RIGHT 3 TIMES |
| 20F | F6 | |
| 210 | F6 | |
| 211 | AE | STORE IN RE.O |
| 212 | EO | SET X=O |
| 213 | 65 | OUT 20 TO SELECT MOST SIG. DIGIT OF EXP. COEFF. |
| 214 | 20 | |
| 215 | E9 | SET X=9 |
| 216 | 6D | INPUT MOST SIG. EXP. COEFF DIGIT |

TABLE I-continued

BOLT GAGE PROGRAM

| ADDRESS | OP CODE | REMARKS |
|---|---|---|
| 217 | FB | } INVERT DATA |
| 218 | FF | |
| 219 | FA | } MASK BITS 4–7 |
| 21A | 0F | |
| 21B | AD | STORE IN LOW RD.O |
| 21C | F8 | |
| 21D | 00 | } SET RC.O & RB.O = OO |
| 21E | AC | |
| 21F | AB | |
| 220 | AA | SET RA.O & R2.O = OO (0400 BCD SUBROUTINE) |
| 221 | A2 | |
| 222 | D2 | SET P = 2 |
| 223 | 30 | } BRANCH TO 30 |
| 224 | 30 | |
| 225 | | } |
| 226 | | |
| 227 | | } SPARE |
| 228 | | |
| 229 | | |
| 22A | | |
| 22B | | } |
| 22C | | |
| 22D | | } SPARE |
| 22E | | |
| 22F | | |
| 230 | F8 | } SET R9.0 = 0D |
| 231 | 0D | |
| 232 | A9 | |
| 233 | F8 | } SET R8.O = 14 |
| 234 | 14 | |
| 235 | A8 | |
| 236 | F8 | |
| 237 | 00 | } STORE OO IN M(0814) VIA R8 |
| 238 | 58 | |
| 239 | 18 | INCREMENT REG. 8 TO (0815) |
| 23A | 72 | GET MEMORY 080D (X+1) |
| 23B | 58 | STORE IN M(0815) |
| 23C | 18 | INCREMENT R8 TO 0816 |
| 23D | 72 | GET MEMORY 080E (X+1) |
| 23E | 58 | STORE IN M(0816) |
| 23F | 18 | INCREMENT R8 TO 0817 |
| 240 | 72 | GET M(080F) & INCREMENT X TO (0810) |
| 241 | 58 | STORE IN LOCATION 0817 |
| 242 | 9F | GET RF.1 (TEMP. DIFF.) |
| 243 | C4 | } NO OPS |
| 244 | C4 | |
| 245 | A3 | PUT IN R3.0 |
| 246 | F8 | } PUT OO IN R4.0, R5.0, R6.0 |
| 247 | 00 | |
| 248 | A4 | |
| 249 | A5 | } PUT OO IN R4.0, R5.0, R6.0 |
| 24A | A6 | |
| 24B | F8 | } PUT 80 IN R1.0 |
| 24C | 80 | |
| 24D | A1 | |
| 24E | D1 | CALL MULTIPLY SUBROUTINE |
| 24F | C4 | } NO OPERATIONS |
| 250 | C4 | |
| 251 | C4 | |
| 252 | 9E | GET RE.1 |
| 253 | FA | } SEPARATE MSB (TEMP. SIGN) |
| 254 | 80 | |
| 255 | 32 | } IF D=0 GO TO 78; OTHERWISE CONTINUE |
| 256 | 78 | |
| 257 | F8 | |
| 258 | 01 | } PUT 01 IN R6.0 |
| 259 | A6 | |
| 25A | F8 | |
| 25B | 0D | } PUT 0D IN R9.0 |
| 25C | A9 | |
| 25D | 72 | } PUT MEMORY 080D IN R5.0 & INCREMENT X |
| 25E | A5 | |
| 25F | 72 | GET MEMORY 080E & INCREMENT X |
| 260 | A4 | 080E→R4.0 |
| 261 | 72 | } 080F→R3.0 |
| 262 | A3 | |
| 263 | F8 | |
| 264 | 17 | } LOAD 17 INTO R9.0 |
| 265 | A9 | |
| 266 | F8 | |
| 267 | 00 | } STORE OO IN 0817 & DECREMENT X |
| 268 | 73 | |
| 269 | 9C | GET RC.1 & STORE IN 0816 & DECREMENT X |
| 26A | 73 | |
| 26B | 9B | GET RB.1 & STOE IN 0815 & DECREMENT X |
| 26C | 73 | |
| 26D | 9A | GET RA.1 & STORE IN 0814 & DECREMENT X |
| 26E | 73 | |
| 26F | F8 | |
| 270 | 80 | } LOAD 80 INTO R1.0 |
| 271 | A1 | |
| 272 | D1 | SET P = 1 – CALL MULTIPLY SUBROUTINE |
| 273 | 3E | IF $\overline{EF3}$ =1, GO TO 90 (LENGTH/STRETCH SWITCH) |
| 274 | 90 | |
| 275 | C0 | |
| 276 | 05 | |
| 277 | 00 | |
| 278 | F8 | |
| 279 | 0F | } STORE 0F IN R9.0 |
| 27A | A9 | |
| 27B | F8 | |
| 27C | 00 | } SUBSTRACT OO – M(080F) |
| 27D | F7 | |
| 27E | A3 | STORE IN R3.0 |
| 27F | 29 | DECREMENT R9 TO 080E |
| 280 | F8 | } SUBTRACT OO- M(080E) & STORE IN R4.O |
| 281 | 00 | |
| 282 | 77 | } SUBSTRACT OO- M(080E) & STORE IN R4.O |
| 283 | A4 | |
| 284 | 29 | DECREMENT R9 TO 080D |
| 285 | F8 | |
| 286 | 00 | } SUBSTRACT OO- M(080D) & STORE IN R5.0 |
| 287 | 77 | |
| 288 | A5 | |
| 289 | 29 | DECREMENT R9 TO 080C |
| 28A | F8 | |
| 28B | 01 | } SUBSTRACT 01-M(080C) & STORE IN R6.O |
| 28C | 77 | |
| 28D | A6 | |

TABLE I-continued
BOLT GAGE PROGRAM

| AD-DRESS | OP CODE | REMARKS |
|---|---|---|
| 28E | 30 | GO TO 63 |
| 28F | 63 | |
| 290 | F8 | LOAD 09 INTO R9.0 |
| 291 | 09 | |
| 292 | A9 | |
| 293 | 72 | LOAD M(0809) INTO D & INCREMENT TO (080A) |
| 294 | BA | STORE IN RA.1 |
| 295 | 72 | LOAD M(080A) INTO RB.1 |
| 296 | BB | |
| 297 | 72 | LOAD M(080B) INTO RC.1 & INCREMENT R9 to 080C |
| 298 | BC | |
| 299 | 7A | SET Q=0 |
| 29A | E0 | SET X=0 |
| 29B | 65 | PUT 10 INTO Z16 SELECTING STRESS FACTOR |
| 29C | 10 | |
| 29D | E9 | SET X=9 |
| 29E | 6D | INPUT MAT. CORR. FACTOR & INVERT (CONTINUATION) |
| 29F | FB | |
| 2A0 | FF | |
| 2A1 | AB | PUT IN RB.0 |
| 2A2 | FA | BLANK 4 MSB'S |
| 2A3 | 0F | |
| 2A4 | AC | STORE IN RC.0 |
| 2A5 | 8B | GET ORIGINAL & SHIFT RIGHT 4 TIMES |
| 2A6 | F6 | |
| 2A7 | F6 | |
| 2A8 | F6 | |
| 2A9 | F6 | |
| 2AA | AB | STORE IN RB.0 |
| 2AB | E0 | SET X=0 |
| 2AC | 65 | PUT 20 IN Z16 SELECTING 3RD DECADE (MSD) |
| 2AD | 20 | |
| 2AE | E9 | SET X=9 |
| 2AF | 6D | INPUT DECADE 3 & INVERT DATA |
| 2B0 | FB | |
| 2B1 | FF | |
| 2B2 | FA | BLANK 4 MSB'S |
| 2B3 | 0F | |
| 2B4 | AA | LOAD INTO RA.0 |
| 2B5 | F8 | |
| 2B6 | 00 | |
| 2B7 | AD | PUT 00 IN RD.0 & RE.0 & RF.0 & R2.0 |
| 2B8 | AE | |
| 2B9 | AF | |
| 2BA | A2 | |
| 2BB | D2 | SET P=2 |
| 2BC | C4 | NO OPS |
| 2BD | C4 | |
| 2BE | C4 | NO OPS |
| 2BF | C4 | |
| 2C0 | F8 | PUT 0C IN R9.0 |
| 2C1 | 0C | |
| 2C2 | A9 | |
| 2C3 | F8 | PUT 14 IN R8.0 |
| 2C4 | 14 | |
| 2C5 | A8 | |
| 2C6 | 72 | LOAD M(080C) & ADVANCE & STORE AT M(0814) |
| 2C7 | 58 | |
| 2C8 | 18 | INCREMENT REGISTER 8 |
| 2C9 | 72 | LOAD M(080D) & ADVANCE & STORE AT M(0815) |
| 2CA | 58 | |
| 2CB | 18 | INCREMENT R8 |
| 2CC | 72 | LOAD M(080E) & ADVANCE & STORE AT M(0816) |
| 2CD | 58 | |
| 2CE | 18 | INCREMENT R8 |
| 2CF | 72 | TRANSFER M(080F) TO M(0817) |
| 2D0 | 58 | |
| 2D1 | 18 | |
| 2D2 | C0 | GO TO 0300 |
| 2D3 | 03 | |
| 2D4 | 00 | |
| 2D5 | | |
| 2D6 | | |
| 2D7 | | |
| 2D8 | | SPARE |
| 2D9 | | |
| 2DA | | |
| 2DB | | |
| 2DC | | |
| 2DD | | |
| 2DE | | |
| 2DF | | |
| 2E0 | | |
| 2E1 | | SPARE |
| 2E2 | | |
| 2E3 | | |
| 2E4 | | |
| 2E5 | | |
| 2E6 | | |
| 2E7 | | |
| 2E8 | | |
| 2E9 | | |
| 2EA | | |
| 2EB | | SPARE |
| 2EC | | |
| 2ED | | |
| 2EE | | |
| 2EF | | |
| 2F0 | | |
| 2F1 | | |
| 2F2 | | |
| 2F3 | | |
| 2F4 | | |
| 2F5 | | |
| 2F6 | | SPARE |
| 2F7 | | |
| 2F8 | | |
| 2F9 | | |
| 2FA | | |
| 2FB | | |
| 2FC | | |
| 2FD | | SPARE |
| 2FE | | |
| 2FF | | |
| 300 | 7A | RESET Q |
| 301 | E0 | SET X=0 |
| 302 | 65 | PUT 01 IN Z16 |
| 303 | 01 | |
| 304 | E9 | SET X=0 |
| 305 | 6D | INPUT & INVERT INITIAL LENGTH DECADES 1 & 2 |
| 306 | FB | |
| 307 | FF | |
| 308 | AE | STORE IN RE.0 |
| 309 | FA | MASK 4 MSB'S & STORE IN RF.0 - 1ST DECADE |
| 30A | 0F | |
| 30B | AF | |
| 30C | 8E | |
| 30D | F6 | |
| 30E | F6 | SHIFT RIGHT 4 PLACES & STORE IN RE.0 |
| 30F | F6 | |
| 310 | F6 | |
| 311 | AE | |
| 312 | E0 | SET X=0 |

TABLE I-continued
BOLT GAGE PROGRAM

| ADDRESS | OP CODE | REMARKS |
|---|---|---|
| 313 | 65 | SET Z16=02 |
| 314 | 02 | |
| 315 | E9 | SET X=9 |
| 316 | 6D | INPUT DATA & INVERT |
| 317 | FB | |
| 318 | FF | |
| 319 | AC | STORE IN RC.O |
| 31A | FA | MASK 4 MSB'S & STORE AT |
| 31B | 0F | RD.O - 3rd DECADE |
| 31C | AD | |
| 31D | 8C | GET RC.O & SHIFT RIGHT |
| 31E | F6 | |
| 31F | F6 | |
| 320 | F6 | SHIFT RIGHT 2 MORE TIMES |
| 321 | F6 | |
| 322 | AC | STORE IN RC.O |
| 323 | E0 | SET X=0 |
| 324 | 65 | SET Z16=04 |
| 325 | 04 | |
| 326 | E9 | SET X=9 |
| 327 | 6D | INPUT & INVERT DECADES |
| 328 | FB | 5 & 6 |
| 329 | FF | |
| 32A | AA | STORE IN RA.O |
| 32B | FA | MASK 4 MSB'S & STORE |
| 32C | 0F | DECADE 5 IN RB.O |
| 32D | AB | |
| 32E | 8A | |
| 32F | F6 | |
| 330 | F6 | SHIFT RIGHT 4 TIMES & |
| 331 | F6 | STORE DECADE 6 IN RA.O |
| 332 | F6 | |
| 333 | AA | |
| 334 | E9 | SET X=9 |
| 335 | F8 | STORE 0F IN R9.O |
| 336 | 0F | |
| 337 | A9 | STORE 0F IN R9.O |
| 338 | F8 | STORE 08 IN R6.O |
| 339 | 08 | |
| 33A | A6 | |
| 33B | F8 | STORE 00 IN M(080F) & |
| 33C | 00 | DECREMENT |
| 33D | 73 | |
| 33E | 26 | DECREMENT R6.O |
| 33F | 86 | GET R6.O |
| 340 | 3A | IF D NOT 0, GO TO 3B |
| 341 | 3B | |
| 342 | 8A | GET RA.O (MOST SIG.DECADE) |
| 343 | 32 | IF D=O, GO TO 57 |
| 344 | 57 | |
| 345 | 2A | DECREMENT RA.O |
| 346 | F8 | SET R9.O=OF |
| 347 | 0F | |
| 348 | A9 | |
| 349 | F8 | |
| 34A | A0 | ADD A0 TO M(080F) & |
| 34B | F4 | DECREMENT R(X) |
| 34C | 73 | |
| 34D | F8 | |
| 34E | 86 | ADD 86 TO M(080E) & |
| 34F | 74 | DECREMENT R(X) |
| 350 | 73 | |
| 351 | F8 | |
| 352 | 01 | ADD 01 TO M(080E) & |
| 353 | 74 | DECREMENT R(X) |
| 354 | 73 | |
| 355 | 30 | GO TO 42 |
| 356 | 42 | |
| 357 | 8B | GET RB.O |
| 358 | 32 | IF D=0, GO TO 6C |
| 359 | 6C | |
| 35A | 2B | DECREMENT RB.O |
| 35B | F8 | |
| 35C | 0F | SET R9.O=OF |
| 35D | A9 | |
| 35E | F8 | LOAD 10 IN D |
| 35F | 10 | |
| 360 | F4 | ADD 10 TO M080F & DECREMENT R(X) |
| 361 | 73 | |
| 362 | F8 | |
| 363 | 27 | ADD 27 TO M080E & |
| 364 | 74 | DECREMENT R(X) |
| 365 | 73 | |
| 366 | F8 | |
| 367 | 00 | COMPLETE MULTIPLE PRECI- |
| 368 | 74 | SION ADDITION |
| 369 | 73 | |
| 36A | 30 | GO TO 57 |
| 36B | 57 | |
| 36C | 8C | GET RC.O |
| 36D | 32 | IF D=O GO TO 81 |
| 36E | 81 | |
| 36F | 2C | DECREMENT RC.O |
| 370 | F8 | |
| 371 | 0F | SET R(X)=OF |
| 372 | A9 | |
| 373 | F8 | |
| 374 | E8 | ADD E8 TO M(080F) & |
| 375 | F4 | DECREMENT X |
| 376 | 73 | |
| 377 | F8 | |
| 378 | 03 | ADD 03 TO M(080E) & |
| 379 | 74 | DECREMENT Y |
| 37A | 73 | |
| 37B | F8 | |
| 37C | 00 | COMPLETE MULTIPLE PRECI- |
| 37D | 74 | SION ADDITION |
| 37E | 73 | |
| 37F | 30 | GO TO 6C |
| 380 | 6C | |
| 381 | 8D | GET RD.O |
| 382 | 32 | IF D=O GO TO 96 |
| 383 | 96 | |
| 384 | 2D | DECREMENT RD.O |
| 385 | F8 | |
| 386 | 0F | SET R(X)=OF |
| 387 | A9 | |
| 388 | F8 | |
| 389 | 64 | ADD 64 TO M(080F) |
| 38A | F4 | |
| 38B | 73 | |

TABLE I-continued
BOLT GAGE PROGRAM

| ADDRESS | OP CODE | REMARKS |
|---|---|---|
| 38C | F8 | |
| 38D | 00 | |
| 38E | 74 | COMPLETE MULTIPLE PRECISION ADDITION |
| 38F | 73 | |
| 390 | F8 | |
| 391 | 00 | COMPLETE MULTIPLE PRECISION ADDITION |
| 392 | 74 | |
| 393 | 73 | |
| 394 | 30 | GO TO 81 TO REPEAT |
| 395 | 81 | |
| 396 | 8E | GET RE.O |
| 397 | 32 | IF D=O GO TO AB |
| 398 | AB | |
| 399 | 2E | DECREMENT RE.O |
| 39A | F8 | |
| 39B | 0F | SET R(X) = 0F |
| 39C | A9 | |
| 39D | F8 | |
| 39E | 0A | ADD 0A TO M(080F) |
| 39F | F4 | |
| 3A0 | 73 | STORE IN M(080F) |
| 3A1 | F8 | |
| 3A2 | 00 | |
| 3A3 | 74 | |
| 3A4 | 73 | COMPLETE MULTIPLE PRECISION ADDITION |
| 3A5 | F8 | |
| 3A6 | 00 | |
| 3A7 | 74 | |
| 3A8 | 73 | |
| 3A9 | 30 | GO TO 96 |
| 3AA | 96 | |
| 3AB | F8 | |
| 3AC | 0F | SET R(X)=0F |
| 3AD | A9 | |
| 3AE | 8F | GET RF.O |
| 3AF | F4 | |
| 3B0 | 73 | |
| 3B1 | F8 | |
| 3B2 | 00 | |
| 3B3 | 74 | ADD LEAST SIG. DIGIT TO TOTAL |
| 3B4 | 73 | |
| 3B5 | F8 | |
| 3B6 | 00 | |
| 3B7 | 74 | |
| 3B8 | 73 | |
| 3B9 | F8 | |
| 3BA | 0F | SET R9.0=0F |
| 3BB | A9 | |
| 3BC | 9C | GET RC.1 |
| 3BD | F7 | SUBTRACT (RC.1)−M(O8OF) |
| 3BE | A3 | STORE IN R3.O |
| 3BF | 29 | DECREMENT R9.O |
| 3C0 | 93 | GET RB.1 |
| 3C1 | 77 | SUBTRACT RB.1−M(080E) |
| 3C2 | A4 | STORE IN R4.O |
| 3C3 | 29 | DECREMENT R9.O |
| 3C4 | 9A | GET RA.1 |
| 3C5 | 77 | SUBTRACT RA.1−M(080D) |
| 3C6 | A5 | STORE IN R5.O |
| 3C7 | 33 | IF DF=1 GO TO DA |
| 3C8 | DA | |
| 3C9 | F8 | |
| 3CA | 0F | SET R(X)=080F |
| 3CB | A9 | |
| 3CC | 9C | GET RC.1 |
| 3CD | F5 | SUBTRACT (M(080F)−RC.1) |
| 3CE | A3 | STORE IN R3.0 |
| 3CF | 29 | DECREMENT R9.0 |
| 3D0 | 9B | GET RB.1 |
| 3D1 | 75 | SUBTRACT WITH BORROW |
| 3D2 | A4 | STORE IN R4.0 |
| 3D3 | 29 | DECREMENT R9.0 |
| 3D4 | 9A | |
| 3D5 | 75 | COMPLETE SUBTRACT |
| 3D6 | A5 | |
| 3D7 | F8 | |
| 3D8 | 7E | PUT 7E IN R7.1 |
| 3D9 | B7 | |
| 3DA | F8 | |
| 3DB | 00 | PUT 00 IN R6.0 |
| 3DC | A6 | |
| 3DD | F8 | |
| 3DE | 80 | PUT 80 IN R1.0 |
| 3DF | A1 | |
| 3E0 | D1 | SET P=1 |
| 3E1 | F8 | |
| 3E2 | 0A | SET R8.0=0A |
| 3E3 | A8 | |
| 3E4 | C0 | |
| 3E5 | 05 | GO TO 0503 |
| 3E6 | 03 | |
| 3E7 | C0 | |
| 3E8 | 00 | GO TO 0000 |
| 3E9 | 00 | |
| 3EA | | |
| 3EB | | |
| 3EC | | |
| 3ED | | |
| 3EE | | |
| 3EF | | SPARE |
| 3F0 | | |
| 3F1 | | |
| 3F2 | | |
| 3F3 | | |
| 3F4 | | |
| 3F5 | | |
| 3F6 | | |
| 3F7 | | |
| 3F8 | | |
| 3F9 | | |
| 3FA | | |
| 3FB | | SPARE |
| 3FC | | |
| 3FD | | |
| 3FE | | |
| 3FF | | |
| 400 | E9 | SET X=9 |
| 401 | F8 | |
| 402 | 10 | SET R9.0=10 |
| 403 | A9 | |
| 404 | F8 | |
| 405 | 05 | R6.0=05 |
| 406 | A6 | |
| 407 | F8 | STORE 00 AT M(R9) |
| 408 | 00 | STORE 00 AT M(29) & DECREMENT R9 |
| 409 | 73 | |
| 40A | 26 | DECREMENT REGISTER 6.0 |
| 40B | 86 | GET R6.0 |
| 40C | 3A | GO TO 07 IF D NOT 0 |
| 40D | 07 | |
| 40E | 8F | GET RF.0 |
| 40F | 32 | IF D=0, GO TO IF |
| 410 | 1F | |
| 411 | 2F | DECREMENT RF |
| 412 | F8 | |
| 413 | 10 | STORE 10 IN R9.0 |
| 414 | A9 | |

TABLE I-continued
BOLT GAGE PROGRAM

| ADDRESS | OP CODE | REMARKS |
|---|---|---|
| 415 | F8 | ADD C7 TO LOCATION M(0810) |
| 416 | C7 | |
| 417 | F4 | |
| 418 | 73 | STORE IN M0810 & DECREMEMT R9 |
| 419 | F8 | ADD 10 TO M(080F) |
| 41A | 10 | |
| 41B | 74 | |
| 41C | | STORE AT 080F & DECREMENT R9 |
| 41D | 30 | GO BACK TO 0E & REPEAT UNTIL RF.0=0 |
| 41E | 0E | |
| 41F | 8E | GET RE.0 |
| 420 | 32 | IF D=0, GO TO 34 |
| 421 | 34 | |
| 422 | 2E | DECREMENT RE.0 |
| 423 | F8 | SET RAM POINTER |
| 424 | 10 | SET RAM POINTER |
| 425 | A9 | |
| 426 | F8 | ADD CONSTANT TO M(0810) |
| 427 | C6 | |
| 428 | F4 | |
| 429 | 73 | |
| 42A | F8 | ADD CONSTANT TO M(080F) |
| 42B | A7 | |
| 42C | 74 | |
| 42D | 73 | |
| 42E | F8 | COMPLETE ADDITION |
| 42F | 00 | |
| 430 | 74 | |
| 431 | 73 | |
| 432 | 30 | GO BACK TO 1F |
| 433 | 1F | |
| 434 | 8D | GET RD.0 (3RD DIGIT) |
| 435 | 32 | IF D=0, GO TO 49 |
| 436 | 49 | |
| 437 | 2D | DECREMENT RD.0 |
| 438 | F8 | SET RAM POINTER AT LEAST SIG. BYTE |
| 439 | 10 | |
| 43A | A9 | |
| 43B | F8 | ADD CONSTANT TO M(0810) |
| 43C | B9 | |
| 43D | F4 | |
| 43E | 73 | |
| 43F | F8 | ADD CONSTANT TO M(080E) |
| 440 | 8D | |
| 441 | 74 | |
| 442 | 73 | ADD CONSTANT TO M(080F) |
| 443 | F8 | ADD CONSTANT TO M(080E) |
| 444 | 06 | |
| 445 | 74 | |
| 446 | 73 | |
| 447 | 30 | GO TO 34 & REPEAT |
| 448 | 34 | |
| 449 | 8C | GET RC.0 (4TH DIGIT) |
| 44A | 32 | IF D=0, GO TO 62 |
| 44B | 62 | |
| 44C | 2C | DECREMENT RC.0 |
| 44D | F8 | SET RAM POINTER AT (0810) |
| 44E | 10 | |
| 44F | A9 | |
| 450 | F8 | ADD CONSTANT TO M(0810) |
| 451 | 38 | |
| 452 | F4 | |
| 453 | 73 | |
| 454 | F8 | ADD CONSTANT TO M(080F) |
| 455 | 89 | |
| 456 | 74 | |
| 457 | 73 | |
| 458 | F8 | ADD CONSTANT TO M(080E) |
| 459 | 41 | |
| 45A | 74 | |
| 45B | 73 | |
| 45C | F8 | COMPLETE MULTIPLE PRECISION ADDITION |
| 45D | 00 | |
| 45E | 74 | |
| 45F | 73 | |
| 460 | 30 | BRANCH TO 49 |
| 461 | 49 | |
| 462 | 8B | GET RB.0 (5TH DIGIT) |
| 463 | 32 | IF D=0, GO TO 7B |
| 464 | 7B | |
| 465 | 2B | DECREMENT RB.0 |
| 466 | F8 | SET RAM POINTER AT M(0810) |
| 467 | 10 | |
| 468 | A9 | |
| 469 | F8 | ADD CONSTANT TO M(0810) |
| 46A | 29 | |
| 46B | F4 | |
| 46C | 73 | |
| 46D | F8 | ADD CONSTANT TO M(080F) |
| 46E | 5C | |
| 46F | 74 | |
| 470 | 73 | |
| 471 | F8 | ADD CONSTANT TO M(080E) |
| 472 | 8F | |
| 473 | 74 | |
| 474 | 73 | |
| 475 | F8 | ADD CONSTANT TO M(080D) |
| 476 | 02 | |
| 477 | 74 | |
| 478 | 73 | |
| 479 | 30 | BRANCH TO 62 |
| 47A | 62 | |
| 47B | 8A | GET RA.0 |
| 47C | 32 | IF D=0, BRANCH TO 94 |
| 47D | 94 | |
| 47E | 2A | DECREMENT RA.0 |
| 47F | F8 | LOAD NEXT ADDRESS |
| 480 | 10 | SET RAM POINTER |
| 481 | A9 | |
| 482 | F8 | ADD CONSTANT TO M(0810) |
| 483 | 9A | |
| 484 | F4 | |
| 485 | 73 | |
| 486 | F8 | ADD CONSTANT TO M(080F) |
| 487 | 99 | |
| 488 | 74 | |
| 489 | 73 | |
| 48A | F8 | ADD CONSTANT TO M(080E) |
| 48B | 99 | |
| 48C | 74 | |
| 48D | 73 | |

TABLE I-continued

BOLT GAGE PROGRAM

| ADDRESS | OP CODE | REMARKS |
|---|---|---|
| 48E | F8 | |
| 48F | 19 | |
| 490 | 74 | ADD CONSTANT TO M(080D) |
| 491 | 73 | |
| 492 | 30 | BRANCH TO 7B TO REPEAT |
| 493 | 7B | |
| 494 | D0 | SET P=O |
| 495 | | |
| 496 | | |
| 497 | | |
| 498 | | SPARE |
| 499 | | |
| 49A | | |
| 49B | | |
| 49C | | |
| 49D | | |
| 49E | | |
| 49F | | |
| 4A0 | | |
| 4A1 | | SPARE |
| 4A2 | | |
| 4A3 | | |
| 4A4 | | |
| 4A5 | | |
| 4A6 | | |
| 4A7 | | |
| 4A8 | | |
| 4A9 | | |
| 4AA | | |
| 4AB | | SPARE |
| 4AC | | |
| 4AD | | |
| 4AE | | |
| 4AF | | |
| 4B0 | | |
| 4B1 | | |
| 4B2 | | |
| 4B3 | | |
| 4B4 | | |
| 4B5 | | SPARE |
| 4B6 | | |
| 4B7 | | |
| 4B8 | | |
| 4B9 | | |
| 4BA | | |
| 4BB | | |
| 4BC | | |
| 4BD | | |
| 4BE | | |
| 4BF | | SPARE |
| 4C0 | | |
| 4C1 | | |
| 4C2 | | |
| 4C3 | | |
| 4C4 | | |
| 4C5 | | |
| 4C6 | | |
| 4C7 | | |
| 4C8 | | |
| 4C9 | | SPARE |
| 4CA | | |
| 4CB | | |
| 4CC | | |
| 4CD | | |
| 4CE | | |
| 4CF | | |
| 4D0 | | |
| 4D1 | | |
| 4D2 | | |
| 4D3 | | SPARE |
| 4D4 | | |
| 4D5 | | |
| 4D6 | | |
| 4D7 | | |
| 4D8 | | |
| 4D9 | | |
| 4DA | | |
| 4DB | | |
| 4DC | | |
| 4DD | | SPARE |
| 4DE | | |
| 4DF | | |
| 4E0 | | |
| 4E1 | | |
| 4E2 | | |
| 4E3 | | |
| 4E4 | | |
| 4E5 | | |
| 4E6 | | |
| 4E7 | | SPARE |
| 4E8 | | |
| 4E9 | | |
| 4EA | | |
| 4EB | | |
| 4EC | | |
| 4ED | | |
| 4EE | | |
| 4EF | | |
| 4F0 | | |
| 4F1 | | SPARE |
| 4F2 | | |
| 4F3 | | |
| 4F4 | | |
| 4F5 | | |
| 4F6 | | |
| 4F7 | | |
| 4F8 | | |
| 4F9 | | |
| 4FA | | |
| 4FB | | SPARE |
| 4FC | | |
| 4FD | | |
| 4FE | | |
| 4FF | | |
| 500 | F8 | |
| 501 | 09 | PUT 09 IN R8.0 |
| 502 | A8 | |
| 503 | 08 | LOAD MEMORY 0809 INTO D |
| 504 | FE | |
| 505 | FE | |
| 506 | FE | SHIFT LEFT 5 TIMES |
| 507 | FE | |
| 508 | FE | |
| 509 | A9 | STORE IN R9.0 |
| 50A | 3B | IF DF=0, GO TO 1C |
| 50B | 1C | |
| 50C | F8 | |
| 50D | 08 | |
| 50E | AF | LOAD 08 IN RF.O & RE.O |
| 50F | AE | |
| 510 | F8 | |
| 511 | 02 | |
| 512 | AD | LOAD 02 IN RD.O & RE.O |
| 513 | AB | |
| 514 | F8 | |
| 515 | 04 | LOAD 04 IN RC.O |
| 516 | AC | |
| 517 | F8 | |
| 518 | 05 | LOAD 05 IN RA.O |
| 519 | AA | |
| 51A | 30 | GO TO 24 (SHORT BRANCH) |
| 51B | 24 | |
| 51C | F8 | |
| 51D | 00 | |
| 51E | AA | LOAD OO IN RA.0 & RB.O |
| 51F | AB | |

TABLE I-continued
BOLT GAGE PROGRAM

| ADDRESS | OP CODE | REMARKS |
|---|---|---|
| 520 | AC | |
| 521 | AD | CONTINUE OO INTO RC.O, |
| 522 | AE | RD.0, RE.0, & RF.0 |
| 523 | AF | |
| 524 | 89 | GET LOW REG. 9.0 |
| 525 | FE | SHIFT LEFT |
| 526 | A9 | STORE IN R9.0 |
| 527 | 3B | IF DF=O, GO TO 3A |
| 528 | 3A | |
| 529 | 1F | |
| 52A | 1F | INCREMENT REGISTER F 4 TIMES |
| 52B | 1F | |
| 52C | 1F | |
| 52D | 1E | |
| 52E | 1E | INCREMENT REGISTER E 4 TIMES |
| 52F | 1E | |
| 530 | 1E | |
| 531 | 1D | INCREMENT REGISTER D 1 TIME |
| 532 | 1C | INCREMENT REGISTER C 2 TIMES |
| 533 | 1C | |
| 534 | 8B | GET RB.O |
| 535 | FC | |
| 536 | 06 | ADD 06 TO B & PUT IN RB.O |
| 537 | AB | |
| 538 | 1A | INCREMENT REGISTER A 2 TIMES |
| 539 | 1A | |
| 53A | 89 | GET LOW REG. 9 |
| 53B | FE | SHIFT LEFT |
| 53C | A9 | PUT IN R9.0 |
| 53D | 3B | IF DF=O, GO TO 4A |
| 53E | 4A | |
| 53F | 1F | INCREMENT RF |
| 540 | 1F | INCREMENT RF |
| 541 | 8E | GET RE.O |
| 542 | FC | |
| 543 | 07 | ADD 07 TO RE & SAVE |
| 544 | AE | |
| 545 | 1C | INCREMENT RC |
| 546 | 1B | |
| 547 | 1B | INCREMENT RB 3 TIMES |
| 548 | 1B | |
| 549 | 1A | INCREMENT R(A) |
| 54A | 89 | GET R9.0 |
| 54B | FE | SHIFT LEFT |
| 54C | A9 | PUT IN R9.0 |
| 54D | 3B | IF DF=O, GO TO 62 |
| 54E | 62 | |
| 54F | 8F | GET RF.O |
| 550 | FC | |
| 551 | 06 | ADD 06 & RESTORE |
| 552 | AF | |
| 553 | 1E | |
| 554 | 1E | INCREMENT RE 3 TIMES |
| 555 | 1E | |
| 556 | 8D | GET RD.O |
| 557 | FC | |
| 558 | 05 | ADD 05 & RESTORE IN RD.O |
| 559 | AD | |
| 55A | 8C | GET RE. RC.O |
| 55B | FC | |
| 55C | 05 | ADD 05 & STORE |
| 55D | AC | |
| 55E | 8B | GET RB.O |
| 55F | FC | ADD 06 & RB.O |
| 560 | 06 | |
| 561 | AB | SAVE IN RB.O |
| 562 | 18 | INCREMENT R8 |
| 563 | 08 | LOAD VIA REGISTER 8 |
| 564 | FE | SHIFT LEFT |
| 565 | A9 | SAVE IN R9.0 |
| 566 | 3B | IF D=O, GO TO 79 |
| 567 | 79 | |
| 568 | 8F | |
| 569 | FC | ADD 08 TO RF.O |
| 56A | 08 | |
| 56B | AF | |
| 56C | 8E | ADD 06 TO RE.O |
| 56D | FC | |
| 56E | 06 | ADD 06 TO RE.O |
| 56F | AE | |
| 570 | 8D | |
| 571 | FC | ADD 07 TO RD.O |
| 572 | 07 | |
| 573 | AD | |
| 574 | 1C | ADD 02 TO RC.O |
| 575 | 1C | |
| 576 | 1B | |
| 577 | 1B | ADD 03 TO RC.O |
| 578 | 1B | |
| 579 | 89 | |
| 57A | FE | SHIFT R9.0 LEFT |
| 57B | A9 | |
| 57C | 3B | IF DF=O, GO TO 8E |
| 57D | 8E | |
| 57E | 1F | ADD 02 TO RF.O |
| 57F | 1F | |
| 580 | 1F | ADD 02 TO RF.O |
| 581 | 1F | |
| 582 | 8E | |
| 583 | FC | |
| 584 | 08 | |
| 585 | AE | ADD 08 TO RE.O |
| 586 | 1D | |
| 587 | 1D | ADD 03 TO RD.O |
| 588 | 1D | |
| 589 | 8C | |
| 58A | FC | |
| 58B | 06 | ADD 06 TO RC.O |
| 58C | AC | |
| 58C | AC | ADD 06 TO RC.O |
| 58D | 1B | ADD 01 TO RB.O |
| 58E | 89 | |
| 58F | FE | SHIFT R9.0 LEFT |
| 590 | A9 | |
| 591 | 3B | IF DF=O, GO TO 9E |
| 592 | 9E | |
| 593 | 1F | ADD 02 TO RF.O |
| 594 | 1F | |
| 595 | 8E | |
| 596 | FC | |
| 597 | 09 | ADD 09 TO RE.O |
| 598 | AE | |
| 599 | 1D | ADD 01 TO RD.O |
| 59A | 8C | |
| 59B | FC | ADD 08 TO RC.O |
| 59C | 08 | |
| 59D | AC | |

TABLE I-continued
BOLT GAGE PROGRAM

| ADDRESS | OP CODE | REMARKS |
|---|---|---|
| 59E | 89 | SHIFT R9.0 LEFT |
| 59F | FE | |
| 5A0 | A9 | SAVE R9.0 |
| 5A1 | 3B | IF DF=0, GO TO AF |
| 5A2 | AF | |
| 5A3 | 8F | |
| 5A4 | FC | ADD 06 TO RF.0 |
| 5A5 | 06 | |
| 5A6 | AF | |
| 5A7 | 8E | |
| 5A8 | FC | ADD 09 TO RE.0 |
| 5A9 | 09 | |
| 5AA | AE | |
| 5AB | 1C | |
| 5AC | 1C | ADD 04 TO RC.0 |
| 5AD | 1C | |
| 5AE | 1C | |
| 5AF | 89 | SHIFT R9.0 LEFT |
| 5B0 | FE | |
| 5B1 | A9 | |
| 5B2 | 3B | IF DF=0, GO TO BE |
| 5B3 | BE | |
| 5B4 | 8F | |
| 5B5 | FC | ADD 08 TO RF.0 |
| 5B6 | 08 | |
| 5B7 | AF | |
| 5B8 | 1E | |
| 5B9 | 1E | ADD 04 TO RE.0 |
| 5BA | 1E | |
| 5BB | 1E | |
| 5BC | 1C | ADD 02 TO RC.0 |
| 5BD | 1C | |
| 5BE | 89 | SHIFT R9.0 LEFT |
| 5BF | FE | |
| 5C0 | A9 | |
| 5C1 | 3B | IF DF=0, GO TO CA |
| 5C2 | CA | |
| 5C3 | 1F | |
| 5C4 | 1F | ADD 04 TO RF.0 |
| 5C5 | 1F | |
| 5C6 | 1F | |
| 5C7 | 1E | ADD 02 TO RE.0 |
| 5C8 | 1E | |
| 5C9 | 1C | ADD 01 TO RC.0 |
| 5CA | 89 | SHIFT R9.0 LEFT |
| 5CB | FE | |
| 5CC | A9 | |
| 5CD | 3B | IF DF=0, GO TO D6 |
| 5CE | D6 | |
| 5CF | 1F | ADD 02 TO RF.0 |
| 5D0 | 1F | |
| 5D1 | 1E | ADD 01 TO RE.0 |
| 5D2 | 8D | |
| 5D3 | FC | ADD 05 TO RD.0 |
| 5D4 | 05 | |
| 5D5 | AD | |
| 5D6 | 89 | SHIFT LEFT R9.0 |
| 5D7 | FE | |
| 5D8 | A9 | |
| 5D9 | 3B | IF DF=0, GO TO E5 |
| 5DA | E5 | |
| 5DB | 8F | |
| 5DC | FC | ADD 06 TO RF.0 |
| 5DD | 06 | |
| 5DE | AF | |
| 5DF | 8E | |
| 5E0 | FC | ADD 05 TO RE.0 |
| 5E1 | 05 | |
| 5E2 | AE | |
| 5E3 | 1D | ADD 02 TO RD.0 |
| 5E4 | 1D | |
| 5E5 | 18 | INCREMENT R8 |
| 5E6 | 08 | INPUT M(080B) |
| 5E7 | FE | SHIFT LEFT |
| 5E8 | A9 | STORE IN R9.0 |
| 5E9 | 3B | IF DF=0, GO TO F2 |
| 5EA | F2 | |
| 5EB | 8F | |
| 5EC | FC | ADD 08 TO RF.0 |
| 5ED | 08 | |
| 5EE | AF | |
| 5EF | 1E | ADD 02 TO RE.0 |
| 5F0 | 1E | |
| 5F1 | 1D | ADD 1 TO RD.0 |
| 5F2 | 89 | SHIFT R9.0 LEFT |
| 5F3 | FE | |
| 5F4 | A9 | |
| 5F5 | E8 | SET X=8 |
| 5F6 | 3B | IF DF=0, GO TO FB |
| 5F7 | FB | |
| 5F8 | C0 | |
| 5F9 | 06 | |
| 5FA | 00 | |
| 5FB | C0 | SPARE |
| 5FC | 06 | |
| 5FD | 08 | |
| 5FE | FF | |
| 5FF | FF | |
| 600 | 1F | |
| 601 | 1F | ADD 04 TO RF.0 |
| 602 | 1F | |
| 603 | 1F | |
| 604 | 8E | |
| 605 | FC | ADD 06 TO RE.0 |
| 606 | 06 | |
| 607 | AE | |
| 608 | 89 | |
| 609 | FE | SHIFT LEFT |
| 60A | A9 | |
| 60B | 3B | IF DF=0, GO TO 12 |
| 60C | 12 | INCREMENT R2 |
| 60D | 1F | ADD 02 to RF.0 |
| 60E | 1F | |
| 60F | 1E | |
| 610 | 1E | ADD 03 TO RE.0 |
| 611 | 1E | |
| 612 | 89 | |
| 613 | FE | SHIFT R9 LEFT |
| 614 | A9 | |
| 615 | 3B | IF DF=0, GO TO 1C |
| 616 | 1C | |

TABLE I-continued
BOLT GAGE PROGRAM

| ADDRESS | OP CODE | REMARKS |
|---|---|---|
| 617 | 8F | |
| 618 | FC | |
| 619 | 06 | ADD 06 TO RF.0 |
| 61A | AF | |
| 61B | 1E | INCREMENT RE.0 |
| 61C | 08 | LOAD MEMORY 080B INTO D |
| 61D | FA | |
| 61E | 0F | MASK BITS 4-7 |
| 61F | 58 | STORE RESULT IN 080B |
| 620 | 8F | |
| 621 | F4 | ADD MEMORY 080B TO RF |
| 622 | AF | |
| 623 | 8F | |
| 624 | FF | SUBTRACT 0A FROM RF |
| 625 | 0A | |
| 626 | 3B | IF DF=0, GO TO 2C |
| 627 | 2C | IF DF=0, GO TO 2C |
| 628 | AF | PUT IN RF.0 |
| 629 | 1E | INCREMENT RE.0 |
| 62A | 30 | GO TO 23 & REPEAT |
| 62B | 23 | |
| 62C | 8E | |
| 62D | FF | SUBTRACT 0A FROM RE.0 |
| 62E | 0A | |
| 62F | 3B | IF DF=0, GO TO 35 |
| 630 | 35 | |
| 631 | AE | PUT IN RE.0 |
| 632 | 1D | INCREMENT RD.0 |
| 633 | 30 | GO TO 2C & REPEAT |
| 634 | 2C | |
| 635 | 8D | |
| 636 | FF | SUBTRACT 0A FROM RD.0 |
| 637 | 0A | |
| 638 | 3B | IF DF=0, GO TO 3E |
| 639 | 3E | |
| 63A | AD | STORE IN RD.0 |
| 63B | 1C | INCREMENT RC.0 |
| 63C | 30 | GO TO 35 & REPEAT |
| 63D | 35 | |
| 63E | 8C | |
| 63F | FF | SUBTRACT 0A FROM RC.0 |
| 640 | 0A | |
| 641 | 3B | IF DF=0, GO TO 47 |
| 642 | 47 | |
| 643 | AC | STORE IN RC.0 |
| 644 | 1B | INCREMENT RB.0 |
| 645 | 30 | GO TO 3E & REPEAT |
| 646 | 3E | |
| 647 | 8B | |
| 648 | FF | SUBTRACT 0A FROM RB |
| 649 | 0A | |
| 64A | 3B | IF DF=0, GO TO 50 |
| 64B | 50 | |
| 64C | AB | STORE IN RB.0 |
| 64D | 1A | INCREMENT RA.0 |
| 64E | 30 | GO TO 47 & REPEAT |
| 64F | 47 | |
| 650 | 30 | GO TO C0 |
| 651 | C0 | |
| 652 | FF | |
| 653 | E0 | SET X=0 |
| 654 | 64 | SELECT OUTPUT 1852 AND |
| 655 | 9A | LOAD 9A INTO REGISTER |
| 656 | 6F | STROBE - INTO DIGIT 1 |
| 657 | 64 | |
| 658 | 8A | INTO DIGIT 2 |
| 659 | 6F | |
| 65A | 64 | |
| 65B | 7A | - INTO DIGIT 3 |
| 65C | 6F | |
| 65D | 64 | |
| 65E | 6A | - INTO DIGIT 4 |
| 65F | 6F | |
| 660 | 64 | |
| 661 | 5A | - INTO DIGIT 5 |
| 662 | 6F | |
| 663 | 64 | |
| 664 | 4A | - INTO DIGIT 5 |
| 665 | 6F | |
| 666 | 64 | |
| 667 | AF | BLANKS COLON |
| 668 | 6F | |
| 669 | C0 | |
| 66A | 00 | BRANCH TO 0004 |
| 66B | 04 | |
| 66C | | |
| 66D | | |
| 66E | | |
| 66F | | |
| 670 | | |
| 671 | | SPARE |
| 672 | | |
| 673 | | |
| 674 | | |
| 675 | | |
| 676 | | |
| 677 | | |
| 678 | | |
| 679 | | |
| 67A | | |
| 67B | | SPARE |
| 67C | | |
| 67D | | |
| 67E | | |
| 67F | | |
| 680 | 6B | INPUT Z15 DATA |
| 681 | FA | SEPARATE ENG/MET CONTROL BIT |
| 682 | 10 | |
| 683 | E0 | SET X=0 |
| 684 | 32 | IF D=0, GO TO 92 |
| 685 | 92 | |
| 686 | 32 | IF SWITCH IS SET FOR LONG |
| 687 | 8E | GO TO 8E ($\overline{EF4}$=0) |
| 688 | 64 | |
| 689 | A1 | LOAD A1 INTO DISPLAY |
| 68A | 6F | |
| 68B | C0 | |
| 68C | 00 | BRANCH TO 0004 |
| 68D | 04 | |
| 68E | 64 | LOAD AD INTO DISPLAY 1802 |
| 68E | AD | |
| 690 | 30 | BRANCH TO 8A |
| 691 | 8A | |
| 692 | 37 | IF LONG, GO TO 98 ($\overline{EF4}$=0) |
| 693 | 98 | |

TABLE I-continued

BOLT GAGE PROGRAM

| ADDRESS | OP CODE | REMARKS |
|---|---|---|
| 694 | 64 | LOAD AD INTO D.P. CONTROL DIGIT |
| 695 | AD | |
| 696 | 30 | BRANCH TO 8A |
| 697 | 8A | |
| 698 | 64 | LOAD AA INTO D.P. CONTROL DIGIT |
| 699 | AA | |
| 69A | 30 | BRANCH TO 8A |
| 69B | 8A | |
| 69C | | |
| 69D | | SPARE |
| 69E | | |
| 69F | | |
| 6A0 | | |
| 6A1 | | |
| 6A2 | | |
| 6A3 | | SPARE |
| 6A4 | | |
| 6A5 | | |
| 6A6 | | |
| 6A7 | | |
| 6A8 | | |
| 6A9 | | |
| 6AA | | |
| 6AB | | |
| 6AC | | |
| 6AD | | |
| 6AE | | SPARE |
| 6AF | | |
| 6B0 | | |
| 6B1 | | |
| 6B2 | | |
| 6B3 | | |
| 6B4 | | |
| 6B5 | | |
| 6B6 | | |
| 6B7 | | |
| 6B8 | | SPARE |
| 6B9 | | |
| 6BA | | |
| 6BB | | |
| 6BC | | |
| 6BD | | |
| 6BE | | SPARE |
| 6BF | | |
| 6C0 | F8 | STORE 01 IN R9.0 |
| 6C1 | 01 | |
| 6C2 | A9 | |
| 6C3 | 8A | GET RA.O & MASK OFF 4MSB'S |
| 6C4 | FA | |
| 6C5 | 0F | |
| 6C6 | 30 | BRANCH TO CF |
| 6C7 | CF | |
| 6C8 | E0 | |
| 6C9 | 64 | |
| 6CA | 9F | |
| 6CB | 6F | |
| 6CC | E9 | SPARE |
| 6CD | 30 | |
| 6CE | D6 | |
| 6CF | E9 | SET X=9 |
| 6D0 | 8F | GET RF.O |
| 6D1 | F9 | OR WITH 90 |
| 6D2 | 90 | |
| 6D3 | 59 | UPDATE DIAPLAY LEAST SIG. DIGIT FROM RF.O |
| 6D4 | 64 | |
| 6D5 | 6F | |
| 6D6 | 8E | |
| 6D7 | F9 | |
| 6D8 | 80 | UPDATE DISPLAY 2ND DIGIT FROM RE.O |
| 6D9 | 59 | |
| 6DA | 64 | |
| 6DB | 6F | UPDATE DISPLAY 2ND DIGIT FROM RE.O |
| 6DC | 8D | |
| 6DD | F9 | |
| 6DE | 70 | |
| 6DF | 59 | UPDATE DISPLAY 3RD DIGIT |
| 6E0 | 64 | |
| 6E1 | 6F | |
| 6E2 | 8C | |
| 6E3 | F9 | |
| 6E4 | 60 | |
| 6E5 | 59 | UPDATE DISPLAY 4TH DIGIT FROM RC.O |
| 6E6 | 64 | |
| 6E7 | 6F | |
| 6E8 | 8B | |
| 6E9 | F9 | |
| 6EA | 50 | |
| 6EB | 59 | UPDATE DISPLAY 5TH DIGIT FROM RB.O |
| 6EC | 64 | |
| 6ED | 6F | |
| 6EE | 97 | GET R7.1 |
| 6EF | 3A | IF D NOT 0, GO TO F5 |
| 6F0 | F5 | |
| 6F1 | 8A | |
| 6F2 | F9 | |
| 6F3 | 40 | UPDATE DISPLAY 6TH DIGIT FROM RA.O |
| 6F4 | C8 | SKIP |
| 6F5 | F8 | |
| 6F6 | 4A | |
| 6F7 | 59 | |
| 6F8 | 64 | UPDATE DISPLAY 6TH DIGIT FROM RA.O |
| 6F9 | 6F | |
| 6FA | 30 | GO TO 80 |
| 6FB | 80 | |
| 6FC | | |
| 6FD | | |
| 6FE | | |
| 6FF | | SPARE |
| 700 | | |
| 701 | | |
| 702 | | |
| 703 | | |
| 704 | | |
| 705 | | |
| 706 | | |
| 707 | | |
| 708 | | SPARE |
| 709 | | |
| 70A | | |
| 70B | | |
| 70C | | |
| 70D | | |
| 70E | | |
| 70F | | |
| 710 | | |
| 711 | | SPARE |
| 712 | | |
| 713 | | |
| 714 | | |
| 715 | | |

TABLE I-continued
BOLT GAGE PROGRAM

| ADDRESS | OP CODE | REMARKS |
|---|---|---|
| 716 | | |
| 717 | | |
| 718 | | |
| 719 | | |
| 71A | | |
| 71B | | SPARE |
| 71C | | |
| 71D | | |
| 71E | | |
| 71F | | |
| 720 | | |
| 721 | | |
| 722 | | |
| 723 | | |
| 724 | | |
| 725 | | SPARE |
| 726 | | |
| 727 | | |
| 728 | | |
| 729 | | |
| 72A | | |
| 72B | | |
| 72C | | |
| 72D | | |
| 72E | | |
| 72F | | SPARE |
| 730 | | |
| 731 | | |
| 732 | | |
| 733 | | |
| 734 | | |
| 735 | | |
| 736 | | |
| 737 | | |
| 738 | | |
| 739 | | SPARE |
| 73A | | |
| 73B | | |
| 73C | | |
| 73D | | |
| 73E | | |
| 73F | | |
| 740 | | |
| 741 | | |
| 742 | | |
| 743 | | SPARE |
| 744 | | |
| 745 | | |
| 746 | | |
| 747 | | |
| 748 | | |
| 749 | | |
| 74A | | |
| 74B | | |
| 74C | | |
| 74D | | SPARE |
| 74E | | |
| 74F | | |
| 750 | | |
| 751 | | |
| 752 | | |
| 753 | | |
| 754 | | |
| 755 | | |
| 756 | | |
| 757 | | SPARE |
| 758 | | |
| 759 | | |
| 75A | | |
| 75B | | |
| 75C | | |
| 75D | | |
| 75E | | |
| 75F | | |
| 760 | | |
| 761 | | SPARE |
| 762 | | |
| 763 | | |
| 764 | | |
| 765 | | |
| 766 | | |
| 767 | | |
| 768 | | |
| 769 | | |
| 76A | | |
| 76B | | SPARE |
| 76C | | |
| 76D | | |
| 76E | | |
| 76F | | |
| 770 | | |
| 771 | | |
| 772 | | |
| 773 | | |
| 774 | | SPARE |
| 775 | | |
| 776 | | |
| 777 | | |
| 778 | | |
| 779 | | |
| 77A | | |
| 77B | | |
| 77C | | SPARE |
| 77D | | |
| 77E | | |
| 77F | | |
| 780 | F8 | SET RAM POINTER = 0.813 |
| 781 | 13 | |
| 782 | A9 | |
| 783 | E9 | SET X = 9 |
| 784 | F8 | STORE 00IN M(R9) & DECREMENT R9 |
| 785 | 00 | |
| 786 | 73 | |
| 787 | 89 | GET R9.0 |
| 788 | FF | SUBTRACT 07 FROM D (12−07) = OB |
| 789 | 07 | |
| 78A | 3A | IF D NOT O, GO TO 84 |
| 78B | 84 | |
| 78C | C4 | NO OPERATION |
| 78D | C4 | |
| 78E | C4 | NO OPERATION |
| 78F | C4 | |
| 790 | F8 | LOAD OF INTO R9.0 |
| 791 | OF | |
| 792 | A9 | |
| 793 | F8 | LOAD 17 INTO R8.0 |
| 794 | 17 | |
| 795 | A8 | |
| 796 | 86 | GET R6.0 |
| 797 | F6 | SHIFT RIGHT |
| 798 | A6 | RELOAD INTO R6.0 |
| 799 | 85 | GET R5.0 |
| 79A | 76 | SHIFT RIGHT |
| 79B | A5 | RELOAD R5.0 |
| 79C | 84 | GET R4.0 |
| 79D | 76 | SHIFT RIGHT |
| 79E | A4 | RELOAD R4.0 |
| 79F | 83 | GET R3.0 |
| 7AO | 76 | SHIFT RIGHT |

TABLE I-continued
BOLT GAGE PROGRAM

| ADDRESS | OP CODE | REMARKS |
|---|---|---|
| 7A1 | A3 | RELOAD INTO R3.0 |
| 7A2 | 3B | } IF DF = O, GO TO C3 |
| 7A3 | C3 | |
| 7A4 | 08 | LOAD M(R8) INTO D |
| 7A5 | F4 | ADD D TO M(080F) |
| 7A6 | 73 | STORE SUM & DECREASE R(R) |
| 7A7 | 28 | DECREMENT R(8) to 0816 |
| 7A8 | 08 | LOAD M(R8) INTO D |
| 7A9 | 74 | ADD WITH CARRY |
| 7AA | 73 | STORE SUM & DECREMENT R9 |
| 7AB | 28 | DECREMENT R(8) TO 0815 |
| 7AC | 08 | LOAD M9R8) INTO D |
| 7AD | 74 | ADD WITH CARRY TO M(080D) |
| 7AE | 73 | STORE SUM DECREMENT R9 |
| 7AF | 28 | DECREMENT R8 TO 0814 |
| 7B0 | 08 | LOAD M(R8) IN D |
| 7B1 | 74 | ADD WITH CARRY TO 080C |
| 7B2 | 73 | STORE SUM DECREMENT R9 |
| 7B3 | 28 | DECREMENT R8 TO 0813 |
| 7B4 | 08 | LOAD M(0813) INTO D |
| 7B5 | 74 | ADD WITH CARRY TO 080B |
| 7B6 | 73 | STORE SUM DECREMENT R9 |
| 7B7 | 28 | DECREMENT R8 TO 0812 |
| 7B8 | 08 | LOAD M(0812) INTO D |
| 7B9 | 74 | ADD WITH CARRY TO 080A |
| 7BA | 73 | STORE SUM DECREMENT R9 |
| 7BB | 28 | DECREMENT R8 TO 0811 |
| 7BC | 08 | LOAD M(0811) INTO D |
| 7BD | 74 | ADD WITH CARRY TO M(0809) |
| 7BE | 73 | STORE SUM DECREMENT R9 |
| 7BF | 28 | DECREMENT R8 TO 0810 |
| 7C0 | 08 | LOAD M(0810) INTO D |
| 7C1 | 74 | ADD TO M(0808) |
| 7C2 | 73 | STORE SUM DECREMENT R9 |
| 7C3 | F8 | } SET R9.0 = 17 |
| 7C4 | 17 | |
| 7C5 | A9 | |
| 7C6 | F0 | } SHIFT LEFT, STORE, DECREMENT R9 TO 0816 |
| 7C7 | FE | |
| 7C8 | 73 | |
| 7C9 | F0 | LOAD |
| 7CA | 7E | } SHIFT LEFT, STORE, DECREMENT R9 TO 0815 |
| 7CB | 73 | |
| 7CC | F0 | } SHIFT LEFT, STORE, DECREMENT R9 TO 0814 |
| 7CD | 7E | |
| 7CE | 73 | |
| 7CF | F0 | } SHIFT LEFT, STORE, DECREMENT R9 TO 0813 |
| 7D0 | 7E | |
| 7D1 | 73 | |
| 7D2 | F0 | } SHIFT LEFT, STORE, DECREMENT R9 TO 0812 |
| 7D3 | 7E | |
| 7D4 | 73 | |
| 7D5 | F0 | } SHIFT LEFT, STORE, DECREMENT R9 TO 0811 |
| 7D7 | 7E | |
| 7D7 | 73 | |
| 7D8 | F0 | } SHIFT LEFT, STORE, DECREMENT R9 TO 0810 |
| 7D9 | 7E | |
| 7DA | 73 | |
| 7DB | F0 | } SHIFT LEFT, STORE, DECREMENT R9 TO 080F |
| 7DC | 7E | |
| 7DD | 73 | |
| 7DE | C4 | NO OPERATION |
| 7DF | 86 | GET LOW 6.0 |
| 7E0 | 3A | } IF D NOT 00, GO TO 90 |
| 7E1 | 90 | |
| 7E2 | 85 | GET LOW 5.0 |
| 7E3 | 3A | } IF D NOT 00, GO TO 90 |
| 7E4 | 90 | |
| 7E5 | 84 | GET LOW 4.0 |
| 7E6 | 3A | } IF NOT 00, GO TO 90 |
| 7E7 | 90 | |
| 7E8 | 83 | GET LOW 3.0 |
| 7E9 | 3A | } IF NOT 00 GO TO 90 |
| 7EA | 90 | |
| 7EB | D0 | SET P = 0 |
| 7EC | F8 | } SET R9.0 POINTER = 080B |
| 7ED | 0B | |
| 7EE | A9 | |
| 7EF | 09 | } SHIFT RIGHT 1 TIME M(080B) |
| 7F0 | F6 | |
| 7F1 | 59 | |
| 7F2 | 19 | INCREMENT R9.0 |
| 7F3 | 09 | } SHIFT RIGHT M(080C) |
| 7F4 | 76 | |
| 7F5 | 59 | |
| 7F6 | 19 | INCREMENT R9.0 |
| 7F7 | 09 | } SHIFT M(080D) RIGHT |
| 7F8 | 76 | |
| 7F9 | 59 | |
| 7FA | 19 | INCREMENT R9.0 |
| 7FB | 09 | } SHIFT M080E RIGHT |
| 7FC | 76 | |
| 7FD | 59 | |
| 7FE | D0 | RETURN TO MAIN PROGRAM |
| 7FF | | SPARE |

I claim:

1. A bolt length measurement apparatus comprising:
an acoustic energy pulse transmitter,
an acoustic energy pulse reciever,
a transducer connected to said transmitter and to said receiver for imparting a transmitted acoustic energy pulse into a bolt and for responding to a reflected echo acoustic energy pulse from a bolt,
a high frequency oscillator for generating a plurality of timing pulses of a constant repetition period,
a couter for counting and registering said timing pulses,
gating means having an input connected to said oscillator, an output connected to said counter, and a gate control terminal connected to said transmitter and receiver for starting said counter in response to a transmitted pulse and stopping said counter in response to a received echo pulse,
calculating means connected to said counter for receiving a registered count indicative of the number of timing pulses counted by said counter between said occurrence of each transmitted pulse and each subsequent received echo pulse,
input factor means connected to said calculating means and providing means for inputting at least one factor into said calculating means,
said calculating means being capable of utilizing said registered timing pulse count and said input factor for generating a signal representative of a length parameter of a bolt,
display means connected to said calculating means for displaying said length parameter,
means for receiving a selected plurality of said pulse counts serially generated by said counter in response to a corresponding plurality of transmitted acoustic energy pulses and received echo pulses, means for determining whether each of said received pulse counts differs from each pulse count received immediately prior thereto by more than a predetermined difference count, means for rejecting said selected plurality of pulse counts and restarting said selected plurality if said predetermined difference count is exceeded, and means for generating said length parameter representative signal based on an average of said plurality of pulse counts when said predetermined difference count is not exceeded for said selected plurality of pulse counts.

2. The apparatus recited in claim 1 wherein said input factor means comprises means for inputting a signal representation of an initial length of a bolt.

3. The apparatus recited in claim 1 wherein said input factor means comprises means for inputting a signal representation of a nominal material velocity factor of a bolt.

4. The apparatus recited in claim 1 wherein said input factor means comprises means for inputting a signal representation of a material velocity correction factor for a bolt subjected to tensile stress.

5. The apparatus recited in claim 1 wherein said input factor means comprises means for inputting a signal representation of a temperature factor indicative of the effects of temperature on the length of a bolt.

6. The apparatus recited in claim 5 wherein said input factor means comprises means for inputting a signal representation of the ambient temperature of said bolt.

7. The apparatus recited in claim 1 wherein said input factor means comprises means for inputting a signal representation of each of the following:
 (a) initial length of a bolt,
 (b) nominal material velocity factor of a bolt,
 (c) material velocity correction factor for a bolt subjected to tensile stress,
 (d) a temperature factor indicative of the effects of temperature on the length of a bolt,
 (e) the ambient temperature of a bolt.

8. The apparatus recited in claim 1 wherein said length parameter may be selected from at least the following two parameters:
 (a) absolute bolt length,
 (b) bolt length stretch relative to initial bolt length.

9. A bolt length measurement apparatus comprising:
an acoustic energy pulse transmitter,
an acoustic energy pulse receiver,
a transducer connected to said transmitter and to said receiver for imparting a transmitted acoustic energy pulse into a bolt and for responding to a reflected echo acoustic energy pulse from a bolt,
a high frequency oscillator for generating a plurality of timing pulses of a constant repetition period,
a counter for counting and registering said timing pulses,
gating means having an input connected to said oscillator, an output connected to said counter, and a gate control terminal connected to said transmitter and receiver for starting said counter in response to a transmitted pulse and stopping said counter in response to a received echo pulse,
calculating means connected to said counter for receiving a registered count indicative of the number of timing pulses counted by said counter between said occurrence of each transmitted pulse and each subsequent received echo pulse,
input factor means connected to said calculating means and providing means for inputting at least one factor into said calculating means,
said calculating means being capable of utilizing said registered timing pulse count and said input factor for generating a signal representative of a length parameter of a bolt,
display means connected to said calculating means for displaying said length parameter,
a received echo pulse detection device having means for detecting when a received echo pulse exceeds a first preset threshold level and having means for detecting when a received echo pulse that has exceeded said first preset threshold level crosses a second present threshold level that is below said first preset threshold level, and having means for generating a signal in response to detection of a received echo pulse that has exceeded said first preset threshold level and has crossed said second preset threshold level.

10. The apparatus recited in claim 9 wherein said input factor means comprises means for inputting a signal representation of an initial length of a bolt.

11. The apparatus recited in claim 9 wherein said input factor means comprises means for inputting a signal representation of a nominal material velocity factor of a bolt.

12. The apparatus recited in claim 9 wherein said input factor means comprises means for inputting a signal representation of a material velocity correction factor for a bolt subjected to tensile stress.

13. The apparatus recited in claim 9 wherein said input factor means comprises means for inputting a signal representation of a temperature factor indicative of the effects of temperature on the length of a bolt.

14. The apparatus recited in claim 9 wherein said input factor means comprises means for inputting a signal representation of the ambient temperature of said bolt.

15. The apparatus recited in claim 9 wherein said input factor means comprises means for inputting a signal representation of each of the following:
 (a) initial length of a bolt,
 (b) nominal material velocity factor of a bolt,
 (c) material velocity correction factor for a bolt subjected to tensile stress,
 (d) a temperature factor indicative of the effects of temperature on the length of a bolt,
 (e) the ambient temperature of a bolt.

16. The apparatus recited in claims 9, 10, 11, 12, 13, 14 or 15 wherein said length parameter may be selected from at least the following two parameters:
 (a) absolute bolt length,
 (b) bolt length stretch relative to initial bolt length.

17. A bolt length measurement apparatus comprising:
an acoustic energy pulse transmitter,
an acoustic energy pulse receiver,
a transducer connected to said transmitter and to said receiver for imparting a transmitted acoustic energy pulse into a bolt and for responding to a reflected echo acoustic energy pulse from a bolt,
a high frequency oscillator for generating a plurality of timing pulses of a constant repetition period,
a counter for counting and registering said timing pulses,
gating means having an input connected to said oscillator, an output connected to said counter, and a gate control terminal connected to said transmitter and receiver for starting said counter in response to a transmitted pulse and stopping said counter in response to a received echo pulse, calculating means connected to said counter for receiving a registered count indicative of the number of timing pulses counted by said counter between said occurrence of each transmitted pulse and each subsequent received echo pulse, input factor means connected to said calculating means and providing means for inputting at least one factor into said calculating means, said calculating means being capable of utilizing said registered timing pulse count and said input factor for generating a signal representative of a length parameter of a bolt, display means connected to said calculating means for displaying said length parameter, means for automatically adjusting the nominal level of receiver gain in accordance with the average magnitude of the previously received echo pulses for a bolt under test, means for linearly increasing the receiver gain between the occurrence of said pulse transmission into a bolt and the occurrence of echo pulse reception from said bolt, and means for suddenly reducing the receiver gain upon the occurrence of echo pulse reception from said bolt.

18. The apparatus recited in claim 17 wherein said input factor means comprises means for inputting a signal representation of an initial length of a bolt.

19. The apparatus recited in claim 17 wherein said input factor means comprises means for inputting a signal representation of a nominal material velocity factor of a bolt.

20. The apparatus recited in claim 17 wherein said input factor means comprises means for inputting a signal representation of a material velocity correction factor for a bot subjected to tensile stress.

21. The apparatus recited in claim 17 wherein said input factor means comprises means for inputting a signal representation of a temperature factor indicative of the effects of temperature on the length of a bolt.

22. The apparatus recited in claim 17 wherein said input factor means comprises means for inputting a signal representation of the ambient temperature of said bolt.

23. The apparatus recited in claim 17 wherein said input factor means comprises means for inputting a signal representation of each of the following:
 (a) initial length of a bolt,
 (b) nominal material velocity factor of a bolt,
 (c) material velocity correction factor for a bolt subjected to tensile stress,
 (d) a temperature factor indicative of the effects of temperature on the length of a bolt,
 (e) the ambient temperature of a bolt.

24. The apparatus recited in claims 17, 18, 19, 20, 21, 22 or 23 wherein said length parameter may be selected from at last the following two parameters:
 (a) absolute bolt length,
 (b) bolt length stretch relative to initial bolt length.

25. An improved apparatus for receiving pulses and for generating a signal representative of reception of a pulse, the apparatus of the type having a pulse amplifier of variable gain and a pulse detector, the improvement comprising:

means for automatically adjusting the nominal level of amplifier gain in accordance with the average magnitude of the previously received pulses, means for linearly increasing the amplifier gain from a preselected time prior to receiving a pulse until a pulse of preselected criteria is detected, means for suddenly reducing the amplifier gain upon detection of a pulse of preselected criteria, said detector having means for detecting when a received pulse exceeds a first preset threshold level and having means for detecting when a received pulse that has exceeded said first preset threshold level crosses a second preset threshold level that is below said first preset threshold level, and having means for generating a signal in response to detection of a received pulse that has exceeded said first preset threshold level and has crossed said second preset threshold level.

26. A bolt length measurement apparatus comprising:
an acoustic energy pulse transmitter,
an acoustic energy pulse receiver,
a transducer connected to said transmitter and to said receiver for imparting a transmitted acoustic energy pulse into a bolt and for responding to a reflected echo acoustic energy pulse from a bolt,
a high frequency oscillator for generating a plurality of timing pulses of a constant repetition period,
a counter for counting and registering said timing pulses,
gating means having an input connected to said oscillator, an output connected to said counter, and a gate control terminal connected to said transmitter and receiver for starting said counter in response to a transmitted pulse and stopping said counter in response to a received echo pulse,
calculaing means connected to said counter for receiving a registered count indicative of the number of timing pulses counted by said counter between said occurrence of each transmitted pulse and each subsequent received echo pulse,
input factor means connected to said calculating means and providing means for inputting at least one factor into said calculating means,
said calculating means being capable of utilizing said registered timing pulse count and said input factor for generating a signal representative of a length parameter of a bolt, and
display means connected to said calculating means for displaying said length parameter,
said acoustic energy pulse receiver having a pulse amplifier of variable gain and a pulse detector,
means for automatically adjusting the nominal level of amplifier gain in accordance with the average magnitude of the previously received pulses,
means for linearly increasing the amplifier gain from a preselected time prior to receiving a pulse until a pulse of preselected criteria is detected,
means for suddenly reducing the amplifier gain upon detection of a pulse of preselected criteria,
said detector having means for detecting when a received pulse exceeds a first preset threshold level and having means for detecting when a received echo pulse that has exceeded said first preset threshold level crosses a second preset threshold level that is below said first preset threshold level, and having means for generating a signal in response to detection of a received echo pulse that has exceeded said first preset threshold level and has crossed said second preset threshold level.

27. The apparatus recited in claim 26 wherein said input factor means comprises means for inputting a signal representation of an initial length of a bolt.

28. The apparatus recited in claim 26 wherein said input factor means comprises means for inpiutting a signal representation of a nominal material velocity factor of a bolt.

29. The apparatus recited in claim 26 wherein said input factor means comprises means for inputting a signal representation of a material velocity correction factor for a bolt subjected to tensile stress.

30. The apparatus recited in claim 26 wherein said input factor means comprises means for inputting a signal representation of a temperature factor indicative of the effects of temperature on the length of a bolt.

31. The apparatus recited in claim 30 wherein said input factor means comprises means for inputting a signal representation of the ambient temperature of said bolt.

32. The apparatus recited in claim 26 wherein said input factor means comprises means for inputting a signal representation of each of the following:
 (a) initial length of a bolt,
 (b) nominal material velocity factor of a bolt,
 (c) material velocity correction factor for a bolt subjected to tensile stress,
 (d) a temperature factor indicative of the effects of temperature on the length of a bolt,
 (e) the ambient air temperature in the proximity of a bolt.

33. The apparatus recited in claims 26, 27, 28, 29, 30, 31, or 32 wherein said length parameter may be selected from at least the following two parameters:
 (a) absolute bolt length,
 (b) bolt length stretch relative to initial bolt length.

34. The apparatus recited in claims 26, 27, 28, 29, 30, 31, or 32 wherein said calculating means comprises:
 means for receiving a selected plurality of said pulse counts serially generated by said counter in response to a corresponding plurality of transmitted acoustic energy pulses and received echo pulses,
 means for determining whether each of said received pulse counts differs from each pulse count received immediately prior thereto by more than a predetermined difference count,
 means for rejecting said selected plurality of pulse counts if said predetermined difference count is exceeded, and
 means for generating said length parameter representative signal based on an average of said plurality of pulse counts when said predetermined difference count is not exceeded for said selected plurality of pulse counts.

35. A method for measuring the length of a bolt, comprising the following steps:
 transmitting an acoustic energy pulse into said bolt,
 receiving an acoustic energy echo pulse from said bolt,
 generating a plurality of timing pulses of a constant repetition period,
 counting said timing pulses,
 starting said counting of timing pulses when said pulse is transmitted,
 stopping said counting of timing pulses when said echo pulse is received,
 calculating the elapsed time corresponding to the number of timing pulses counted,
 modifying said elapsed time by an input factor,
 displaying a length parameter of said bolt based on said modified elapsed time,
 detecting when the received echo pulse exceeds a first preset threshold level and when a received echo pulse crosses a second preset threshold level that is below said first preset threshold level, and
 generating a signal in response to detection of a received echo pulse that first exceeds said first preset threshold level and then crosses said second preset threshold level.

36. The method recited in claim 35 wherein said input factor modifying step includes the step of modifying said elapsed time by a factor dependent on the initial length of said bolt.

37. The method recited in claim 35 wherein said input factor modifying step includes the step of modifying said elapsed time by a factor dependent on a nominal velocity factor of said bolt.

38. The method recited in claim 35 wherein said input factor modifying step includes the step of modifying said elapsed time by a factor dependent on a material velocity correction factor for a bolt subjected to tensile stress.

39. The method recited in claim 35 wherein said input factor modifying step includes the step of modifying said elapsed time by a factor dependent upon the effect of temperature on the length of said bolt.

40. The method recited in claim 35 wherein said input factor modifying step includes the step of modifying said elapsed time by a factor dependent upon the ambient temperature of said bolt.

41. The method recited in claim 35 wherein said input factor modifying step includes the step of modifying said elapsed time by a factor dependent upon each of the following:
 (a) initial length of a bolt,
 (b) nominal material velocity factor of a bolt,
 (c) material velocity correction factor for a bolt subjected to tensile stress,
 (d) a temperature factor indicative of the effects of temperature on the length of a bolt,
 (e) the ambient temperature of a bolt.

42. A method for measuring the length of a bolt, comprising the following steps:
 transmitting an acoustic energy pulse into said bolt,
 receiving an acoustic energy echo pulse from said bolt,
 generating a plurality of timing pulses of a constant repetition period,
 counting said timing pulses,
 starting said counting of timing pulses when said pulse is transmitted,
 stopping said counting of timing pulses when said echo pulse is received,
 calculating the elapsed time corresponding to the number of timing pulses counted,
 modifying said elapsed time by an input factor, and
 displaying a length parameter of said bolt based on said modified elapsed time,
 applying gain to said received echo pulse, said gain being varied in accordance with the following:
 (a) setting a nominal gain level in accordance with the average magnitude of previously received echo pulses for a bolt under test, (b) linearly increasing gain level between the occurrence of said pulse transmission into a bolt and the occurrence of echo pulse reception from said bolt, and (c) reducing gain level upon the occurrence of echo pulse reception from said bolt.

43. The method recited in claim 42 wherein said input factor modifying step includes the step of modifying said elapsed time by a factor dependent on the initial length of said bolt.

44. The method recited in claim 42 wherein said input factor modifying step includes the step of modifying said elapsed time by a factor dependent on a nominal velocity factor of said bolt.

45. The method recited in claim 42 wherein said input factor modifying step includes the step of modifying said elapsed time by a factor dependent on a material velocity correction factor for a bolt subjected to tensile stress.

46. The method recited in claim 42 wherein said input factor modifying step includes the step of modifying said elapsed time by a factor dependent upon the effect of temperature on the length of said bolt.

47. The method recited in claim 42 wherein said input factor modifying step includes the step of modifying said elapsed time by a factor dependent upon the ambient temperature of said bolt.

48. The method recited in claim 42 wherein said input factor modifying step includes the step of modifying said elapsed time by a factor dependent upon each of the following:

(a) initial length of a bolt,
(b) nominal material velocity factor of a bolt,
(c) material velocity correction factor for a bolt subjected to tensile stress,
(d) a temperature factor indicative of the effects of temperature on the length of a bolt,
(e) the ambient temperature of a bolt.

49. An apparatus for measuring a dimension of a test specimen, comprising:

an acoustic energy pulse transmitter,
an acoustic energy pulse receiver,
a transducer connected to said transmitter and to said receiver for imparting a transmitted acoustic energy pulse into said test specimen and for responding to a reflected echo acoustic energy pulse from said test specimen,
a high frequency oscillator for generating a plurality of timing pulses of a constant repetition period,
a counter for counting and registering said timing pulses,
gating means having an input connected to said oscillator, an output connected to said counter, and a gate control terminal connected to said transmitter and receiver for starting said counter in response to a transmitted pulse and stopping said counter in response to a received echo pulse,
calculating means connected to said counter for receiving a registered count indicative of the number of timing pulses counted by said counter between said occurrence of each transmitted pulse and each subsequent received echo pulse,
input factor means connected to said calculating means and providing means for inputting at least one factor into said calculating means,
said calculating means being capable of utilizing said registered timing pulse count and said input factor for generating a signal representative of a dimensional parameter of said test specimen,
display means connected to said calculating means for displaying said dimensional parameter,
means for receiving a selected plurality of said pulse counts serially generated by said counter in response to a corresponding plurality of transmitted acoustic energy pulses and received echo pulses,
means for determining whether each of said received pulse counts differs from each pulse count received immediately prior thereto by more than a predetermined difference count,
means for rejecting said selected plurality of pulse counts and restarting said selected plurality if said predetermined difference count is exceeded, and
means for generating said dimensional parameter representative signal based on an average of said plurality of pulse counts when said predetermined difference count is not exceeded for said selected plurality of pulse counts.

50. An apparatus for measuring a dimension of a test specimen, comprising:

an acoustic energy pulse transmitter,
an acoustic energy pulse receiver,
a transducer connected to said transmitter and to said receiver for imparting a transmitted acoustic energy pulse into said test specimen and for responding to a reflected echo acoustic energy pulse from said test specimen,
a high frequency oscillator for generating a plurality of timing pulses of a constant repetition period,
a counter for counting and registering said timing pulses,
gating means having an input connected to said oscillator, an output connected to said counter, and a gate control terminal connected to said transmitter and receiver for starting said counter in response to a transmitted pulse and stopping said counter in response to a received echo pulse,
calculating means connected to said counter for receiving a registered count indicative of the number of timing pulses counted by said counter between said occurrence of each transmitted pulse and each subsequent received echo pulse,
input factor means connected to said calculating means and providing means for inputting at least one factor into said calculating means,
said calculating means being capable of utilizing said registered timing pulse count and said input factor for generating a signal representative of a dimensional parameter of said test specimen,
display means connected to said calculating means for displaying said dimensional parameter,
a received echo pulse detection device having means for detecting when a received echo pulse exceeds a first preset threshold level and having means for detecting when a received echo pulse that has exceeded said first preset threshold level crosses a second preset threshold level that is below said first preset threshold level, and having means for generating a signal in response to detection of a received echo pulse that has exceeded said first preset threshold level and has crossed said second preset threshold level.

51. An apparatus for measuring a dimension of a test specimen, comprising:

an acoustic energy pulse transmitter,
and acoustic energy pulse receiver, a transducer connected to said transmitter and to said receiver for imparting a transmitted acoustic energy pulse into said test specimen and for responding to a reflected echo acoustic energy pulse from said test specimen, a high frequency oscillator for generating a plurality of timing pulses of a constant repetition period, a counter for counting and registering said timing pulses, gating means having an input connected to said oscillator, an output connected to said counter, and a gate control terminal connected to said transmitter and receiver for starting said counter in response to a transmitted pulse and stopping said counter in response to a received echo pulse, calculating means connected to said counter for receiving a registered count indicative of the number of timing pulses counted by said counter between said occurrence of each transmitted pulse and each subsequent received echo pulse, input factor means connected to said calculating means and providing means for inputting at least one factor into said calculating means, said calculating means being capable of utilizing said registered timing pulse count and said input factor for generating a signal representative of a dimensional parameter of said test specimen, display means connected to said calculating means for displaying said dimensional parameter, means for automatically adjusting the nominal level of receiver gain in accordance with the average magnitude of the previously received echo pulses for said test specimen under test, means for linearly increasing the receiver gain between the occurrence of said pulse transmission into said test specimen and the occurrence of echo pulse reception from said test specimen, and means for suddenly reducing the receiver gain upon the occurrence of echo pulse reception from said test specimen.

* * * * *